United States Patent
Castro

(10) Patent No.: US 8,226,718 B2
(45) Date of Patent: *Jul. 24, 2012

(54) SPINAL IMPLANT AND METHOD OF USING SPINAL IMPLANT

(75) Inventor: Frank Castro, Louisville, KY (US)

(73) Assignee: Cardinal Spine, LLC, Louisville, KY (US)

( * ) Notice: Subject to any disclaimer, the term of this patent is extended or adjusted under 35 U.S.C. 154(b) by 769 days.

This patent is subject to a terminal disclaimer.

(21) Appl. No.: 12/290,069

(22) Filed: Oct. 27, 2008

(65) Prior Publication Data

US 2010/0324679 A1    Dec. 23, 2010

Related U.S. Application Data

(63) Continuation-in-part of application No. 12/221,779, filed on Aug. 6, 2008, now Pat. No. 8,002,832, which is a continuation of application No. 11/089,103, filed on Mar. 24, 2005, now Pat. No. 7,435,261.

(51) Int. Cl.
*A61F 2/44* (2006.01)

(52) U.S. Cl. .................................................. 623/17.11

(58) Field of Classification Search ..... 623/17.11–17.16
See application file for complete search history.

(56) References Cited

U.S. PATENT DOCUMENTS

| | | | |
|---|---|---|---|
| 4,892,545 A * | 1/1990 | Day et al. ................... | 623/17.11 |
| 5,147,402 A | 9/1992 | Bohler et al. | |
| 5,192,327 A | 3/1993 | Brantigan | |
| 5,405,391 A * | 4/1995 | Hednerson et al. ......... | 623/17.15 |
| 5,425,772 A | 6/1995 | Brantigan | |
| 5,522,899 A * | 6/1996 | Michelson ..................... | 606/279 |
| 5,558,674 A | 9/1996 | Heggeness et al. | |
| 5,609,635 A | 3/1997 | Michelson | |
| 5,766,252 A | 6/1998 | Henry et al. | |
| 6,066,175 A | 5/2000 | Henderson et al. | |
| 6,080,193 A | 6/2000 | Hochshuler et al. | |
| 6,090,143 A | 7/2000 | Meriwether et al. | |
| 6,117,174 A | 9/2000 | Nolan | |
| 6,159,245 A | 12/2000 | Meriwether et al. | |
| 6,231,610 B1 | 5/2001 | Geisler | |
| 6,287,343 B1 | 9/2001 | Kuslich et al. | |
| 6,302,914 B1 * | 10/2001 | Michelson ................. | 623/17.16 |
| 6,395,030 B1 | 5/2002 | Songer et al. | |
| 6,395,035 B2 | 5/2002 | Bresina et al. | |
| 6,409,766 B1 | 6/2002 | Brett | |
| 6,432,107 B1 | 8/2002 | Ferree | |
| 6,491,724 B1 | 12/2002 | Ferree | |
| 6,537,320 B1 | 3/2003 | Michelson | |

(Continued)

OTHER PUBLICATIONS

Barack, R. L. Revision Total Hip Arthroplasty: The Femoral Component. J. Am Acad Orthop Surg 1995; 3(2); 79-85. USA.

(Continued)

*Primary Examiner* — Eduardo C Robert
*Assistant Examiner* — Jerry Cumberledge
(74) *Attorney, Agent, or Firm* — Kenneth F. Pearce

(57) ABSTRACT

The present invention is a brace or spinal implant that can be inserted into vertebra that has had a cavity surgically created therein. The trapezoidal shaped spinal implant includes an opening that allows the surgical team to view the dura mater prior to packing the implant with osteogenic substances. Embodiments of the current invention can include brakes, superior and inferior plates which assist with the fixation of the implant to vertebral bone.

23 Claims, 13 Drawing Sheets

U.S. PATENT DOCUMENTS

| | | | |
|---|---|---|---|
| 6,569,201 B2 | 5/2003 | Moumene et al. | |
| 6,576,016 B1 | 6/2003 | Hochshuler et al. | |
| 6,641,614 B1 | 11/2003 | Wagner et al. | |
| 6,660,038 B2 | 12/2003 | Bayer, II et al. | |
| 6,712,825 B2 | 3/2004 | Aebi et al. | |
| 6,712,852 B1 | 3/2004 | Chung et al. | |
| 6,746,484 B1 | 6/2004 | Lin et al. | |
| 6,761,738 B1 | 7/2004 | Boyd | |
| 6,767,367 B1 | 7/2004 | Michelson | |
| 6,776,798 B2 | 8/2004 | Camino et al. | |
| 6,805,714 B2 | 10/2004 | Sutcliffe | |
| 6,808,538 B2 | 10/2004 | Paponneau | |
| 6,837,905 B1 * | 1/2005 | Lieberman | 623/17.16 |
| 6,863,673 B2 | 3/2005 | Gerbec et al. | |
| 6,926,737 B2 | 8/2005 | Jackson et al. | |
| 6,942,697 B2 | 9/2005 | Lange et al. | |
| 6,997,953 B2 | 2/2006 | Chung et al. | |
| D524,942 S | 7/2006 | Felix | |
| 7,166,110 B2 | 1/2007 | Yundt | |
| 7,182,782 B2 * | 2/2007 | Kirschman | 623/17.11 |
| 7,232,463 B2 | 6/2007 | Falahee | |
| 7,435,261 B1 * | 10/2008 | Castro | 623/17.11 |
| 7,618,460 B2 * | 11/2009 | Boyd | 623/17.16 |
| 7,641,701 B2 | 1/2010 | Kirschman | |
| 7,942,932 B2 * | 5/2011 | Castro | 623/17.11 |
| 8,002,832 B2 * | 8/2011 | Castro | 623/17.11 |
| 2002/0128652 A1 * | 9/2002 | Ferree | 606/61 |
| 2003/0125739 A1 | 7/2003 | Bagga et al. | |
| 2004/0064184 A1 | 4/2004 | Chung et al. | |
| 2004/0073314 A1 | 4/2004 | White et al. | |
| 2004/0126407 A1 | 7/2004 | Falahee | |
| 2004/0153155 A1 | 8/2004 | Chung et al. | |
| 2004/0153160 A1 | 8/2004 | Carrasco | |
| 2004/0199256 A1 * | 10/2004 | Wang | 623/17.12 |
| 2004/0204714 A1 | 10/2004 | Liu et al. | |
| 2004/0225360 A1 | 11/2004 | Malone | |
| 2005/0071006 A1 | 3/2005 | Kirschman | |
| 2005/0071008 A1 | 3/2005 | Kirschman | |
| 2005/0149192 A1 | 7/2005 | Zucherman et al. | |
| 2005/0159813 A1 | 7/2005 | Molz, IV et al. | |
| 2006/0287725 A1 | 12/2006 | Miller | |
| 2007/0016295 A1 | 1/2007 | Boyd | |
| 2007/0129805 A1 | 6/2007 | Braddock | |
| 2007/0255409 A1 | 11/2007 | Dickson et al. | |
| 2007/0255413 A1 | 11/2007 | Edie et al. | |
| 2008/0015694 A1 | 1/2008 | Tribus | |
| 2008/0021476 A1 | 1/2008 | Kirschman | |
| 2008/0132901 A1 | 6/2008 | Recoules-arche et al. | |
| 2008/0154377 A1 * | 6/2008 | Voellmicke | 623/17.16 |
| 2008/0275506 A1 | 11/2008 | Baynham | |
| 2009/0036985 A1 | 2/2009 | Whiting | |
| 2009/0234364 A1 | 9/2009 | Crook | |
| 2010/0004752 A1 | 1/2010 | White et al. | |

OTHER PUBLICATIONS

Castro, F. P., Jr. Stingers, Cervical Cord Neurapraxia, and Stenosis. Clin Sport Med 2003; 22: 483-492. USA.

Majd M.E, Vadhva, M., Holt R.T. Anterior Cervical Reconstruction Using Titanium Cages With Anterior Plating. Spine 1999; 24 (15): 1604-1610. USA.

Park J.B., Cho Y.S., Riew, K.D. Development of Adjacent-Level Ossification in Patient with an Anterior Cervical Plate. J. Bone Surg. 1005; 87-A: 558-563. USA.

* cited by examiner

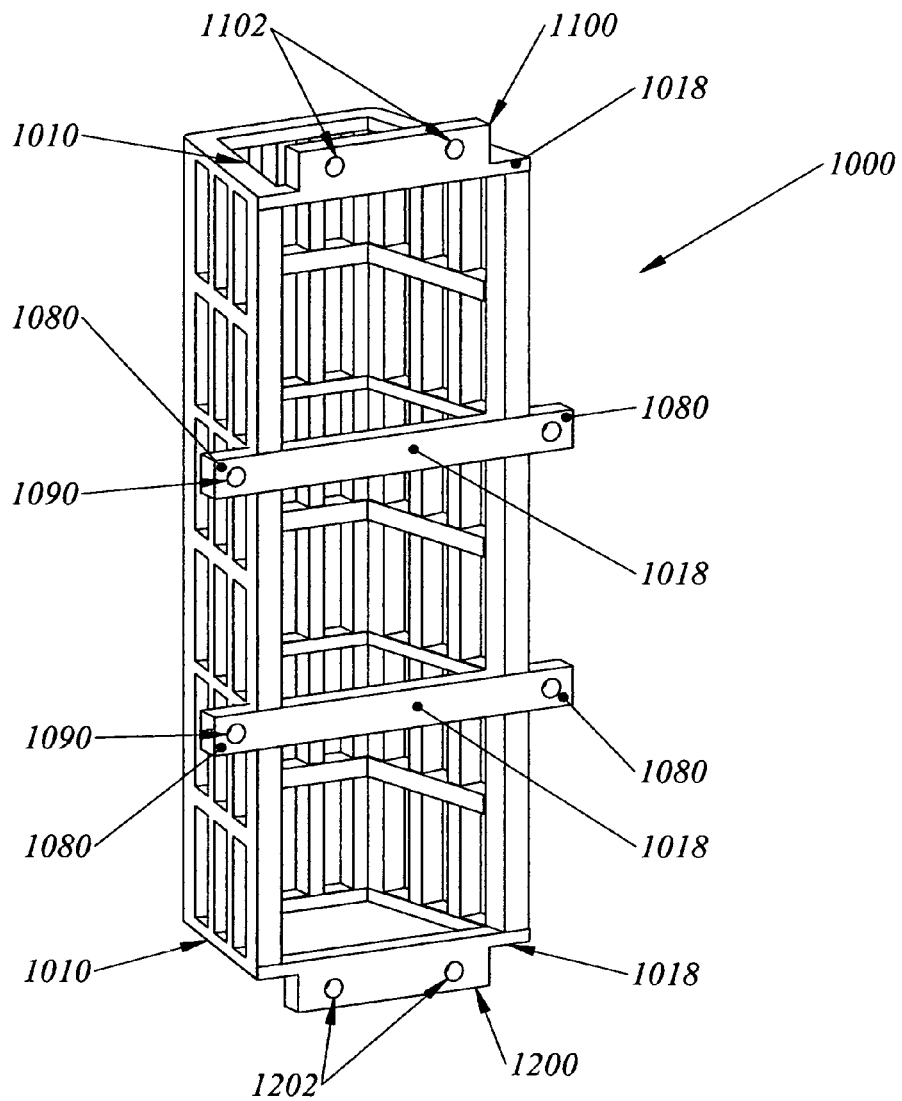
*FIG. 15*
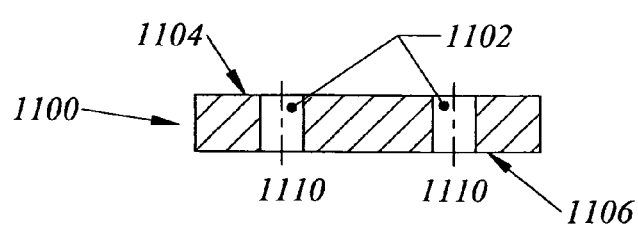
*FIG. 16*
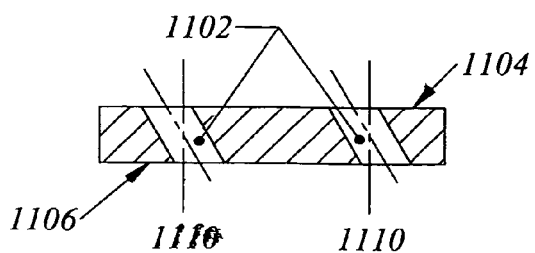

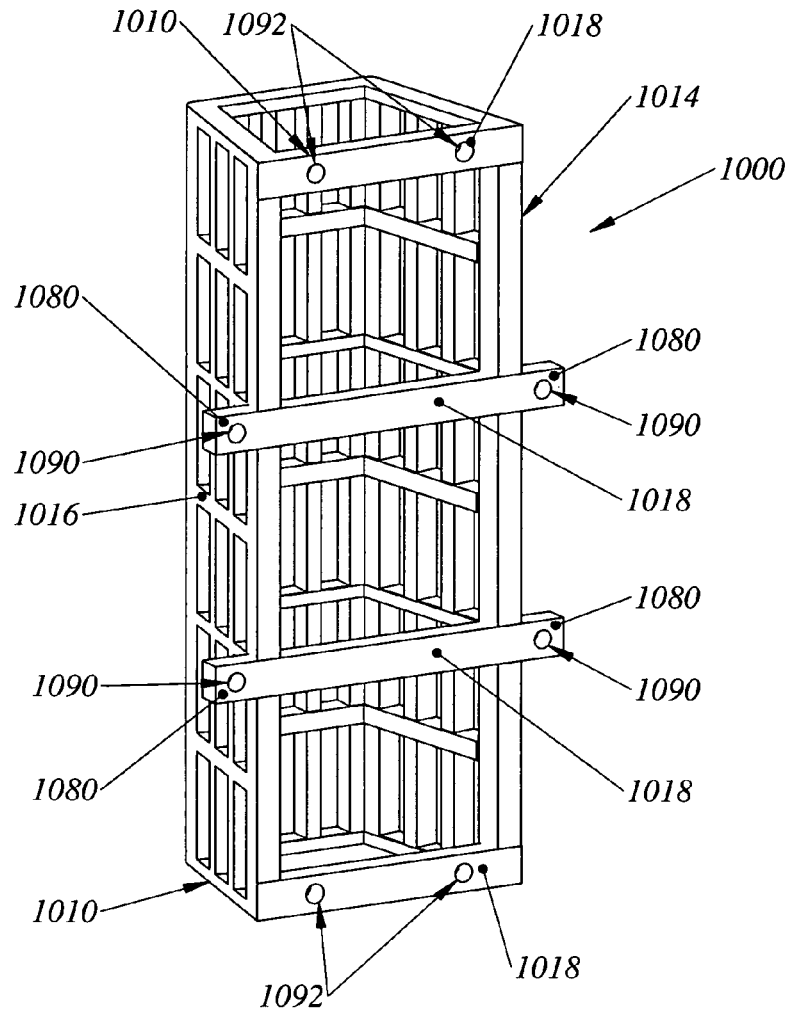
FIG. 17
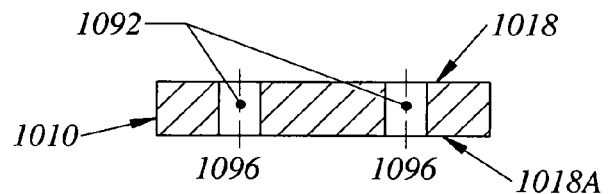
FIG. 18
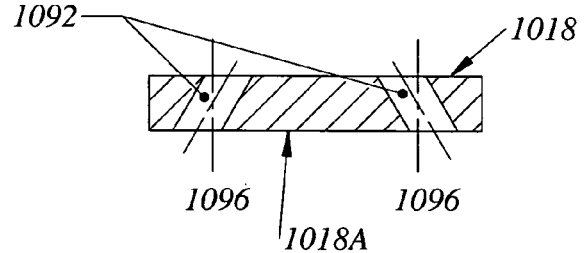

SPINAL IMPLANT AND METHOD OF USING SPINAL IMPLANT

This Application is a Continuation-In-Part of Application for Letters Patent, Ser. No. 12/221,779, entitled—Spinal Method and Method of Using Spinal Implant—filed on Aug. 6, 2008 now U.S. Pat. No. 8,002,832 that is a continuation of Application for Letters Patent, Ser. No. 11/089,103, entitled—Spinal Method and Method of Using Spinal Implant—filed on Mar. 24, 2005, now U.S. Pat. No. 7,435,261 B2 issued Oct. 14, 2008.

BACKGROUND OF THE INVENTION

1. Field of the Invention

Among other things, the present invention is related to a surgical brace or implant that can be inserted into a cavity that has been created by removing at least a part of one or more vertebra. The generally trapezoidal shaped brace can be supplied as a single receptacle or a span of conjoined receptacles. Each receptacle is provided with an opening that allows the surgical team to view the dura mater prior to packing the receptacle with osteogenic substances. One or more brakes can be incorporated into the spinal implant, and the brakes can include bores for receiving fasteners. Other embodiments of the current implant are provided with superior and inferior plates having bores that can receive fasteners.

2. Description of the Previous Art

1) US Publish Patent Application No. 2003/0125739 A1-Bagga, et al. discloses a bioactive spinal implant and method of manufacture. Among other things, it does not appear that the Bagga invention practices the use of posts, supports or ties.

2) U.S. Pat. No. 6,767,367 B1-Michelson enables a spinal fusion implant having deployable bone engaging projections. Michelson teaches that the '367 implant 300 has a rotatable member 320 that is preferably frustoconical in shape. Rotatable member 320 has bone engaging projections 332 adapted to penetrably engage the bone of the adjacent vertebral bodies. Bone engaging projections 332 are preferably configured such that in a retracted position, implant 300 may be linearly inserted into the disc space. After implant 300 is inserted into the disc space, bone engaging projections 332 are moved to a deployed position to penetrably engage the endplates of each adjacent vertebral body and prevent the expulsion of implant 300 from the disc space.

3) U.S. Pat. No. 6,537,320 B1-Michelson enables a self-broaching, rotable, push-in interbody spinal fusion implant and method for its deployment. Among other things, it does not appear that the Michelson invention practices the use of posts, supports or ties.

4) U.S. Pat. No. 5,609,635-Michelson enables a lordotic interbody spinal fusion implant. The Michelson Summary of the Invention teaches that the '635 modular implants are generally wedge-shaped that have upper and lower surfaces conforming to the contours of the vertebral endplates, which contours include but are not limited to being relatively flat or convex. Michelson states, "As the disc spaces in the lumbar spine are generally lordotic, said implants in the preferred embodiment would be taller anteriorly, that is at the implant's insertion end, and less tall posteriorly, that is at the implant's trailing end. To introduce an implant that is taller at its insertion end than the space available at the posterior aspect of the disc space, even when that disc space is optimally distracted, is problematic."

5) U.S. Pat. No. 6,302,914 B1-Michelson enables a lordotic interbody spinal fusion implant. The '914 Patent is a continuation Patent of the U.S. Pat. No. 5,609,635-Michelson Patent.

6) U.S. Pat. No. 6,066,175-Henderson, et al. enables a fusion stabilization chamber. Mesh cage 41 sits between vertebral bodies 43 and 45. Intervertebral discs 46and 47 flank the vertebral bodies. The spinal cord is indicated by reference numeral 53. Cage 41 fills the space previously occupied by another such disc. The cage includes barrel vaults 48 and 49, and has flanges 50 and 51 which help to anchor the cage on the vertebral bodies and provide means for attachment thereto. The Henderson flanges also prevent the cage from being inadvertently tapped into the spinal cord, and they also distribute the shear and bending moment and thus increase the stability of the device. The flanges also provide one or more additional holes to accommodate more screws for affixing the device to the vertebral bodies. Both the flanges and barrel vaults are preferably integral with the cage. The barrel vaults can be either threaded or non-threaded. The screws which are inserted through the barrel vaults are preferably of the locking type, so that they lock into the barrel vaults when fully inserted. The cage is preferably rectangular when viewed from the top or the bottom. The cage may be constructed such that the bottom (the side pointed towards the spinal cord) is solid and not made of mesh. The top of the cage could also be solid. A mesh structure is most necessary on the sides of the cage, where the cage abuts the vertebral bodies, so as to promote fusion between the bone chips or bone substitute material inside the cage and the adjacent vertebral bodies.

7) U.S. Pat. No. 5,766,252-Henry, et al. enables an interbody spinal prosthetic implant and method. Among other things, the Henry device practices threaded hole 38 and longitudinal struts 84.

8) U.S. Pat. No. 5,425,772-Brantigan enables a prosthetic implant for intervertibral spinal fusion. Among other things, the '772 device practices traverse teeth or serrations 19 where the teeth have sharp peaks 19a, slopping walls 19b and valleys 19c.

9) U.S. Pat. No. 5,147,402-Bohler, et al. enables an implant for ingrowth of osseous tissue. Among other things, Bohler does not appear to practice a generally wedge shaped cage.

10) U.S. Pat. No. 6,746,484-Liu, et al. enables a spinal implant. Among other things, the Liu disclosure teaches that tool 22 has a milling cutter 23, central cutting portion 24 and two non-cutting portions 31, 36 arranged at opposite ends of central cutting portion 24. Non-cutting portions 31, 36 have height h corresponding to the intersomatic space and permitting uniform, symmetrical cutting of a predetermined length through a central region of both vertebral plates 15, 16. The geometry of portions 24, 31, 36 is determined for preparing the intersomatic space with the geometry of implant 1 to restore the natural lordosis of the intervertebral space, and correspondingly the distances represented by h and d1 are approximately equal.

11) U.S. Pat. No. 6,231,610 B1-Geisler enables an anterior cervical column support device. The '610 apparatus utilizes serrations on the load bearing surfaces and two screw holes.

12) U.S. Pat. No. 6,660,038 B2-Boyer, et al. enables skeletal reconstruction cages. The Boyer Patent discloses an end cap 210 suitable for coupling to central shaft 160 includes an outer wall 212, as well as a central hole disposed along axis 213 with a lower inner wall 214, an upper inner wall 216, and an inner ridge portion 218. Lower inner wall 214 extends about a depth $H_2$ and is sized to fit snugly on an upper or lower portion 182, 184 of central shaft 160 with an upper or lower face 162, 164 abutting a shoulder 218. Preferably, upper inner wall 216 has a dimension that is about the same as dimension $D_5$ of hole 178 of central shaft 160. End cap 210 is symmetrical about line 220, and is generally oblong in shape with first and second widths $W_2$, $W_3$. Notably, while outer wall 176 of central shaft 160 is generally circular, outer wall 212 of end cap 210 is generally oblong, so that a generally I-shaped skeletal reconstruction cage may be formed when a pair of end caps 210 are placed on central shaft 160.

13) U.S. Pat. No. 6,491,724-Ferree enables a spinal fusion cage with lordosis correction. Among other things, the '724 Patent teaches, "In the preferred embodiment, the anterior portion 112 includes mating members 120 and 122 with teeth 124 or other features to form a locking or ratchet mechanism, as shown. Whatever apparatus is used, the purpose is to maintain the height of the anterior portion of the cage at a desired level consistent with lordosis upon installation."

14) U.S. Pat. No. 6,117,174-Nolan enables a spinal implant device. Among other things, the '174 apparatus utilizes disc 14 made of the same material as body 12. Inner surfaces of legs 18 and 20 are curved.

SUMMARY OF THE INVENTION

Unlike traditional spinal implants, the present invention provides a spinal implant that can be packed with bone graft and/or other osteogenic materials or substances after the spinal implant has been inserted into a surgically created cavity of one or more vertebra. Prior to packing the receptacle with osteogenic substances, the surgical team can view the dura mater of the spinal cord. When inserting the brace, during a surgical procedure, the wedge-like shape of the implant assists the surgical team in not impinging the spinal cord with the brace. Post operative and prior to complete arthrodesis, the generally wedge-like shape of the implant inhibits extrusion of the brace against the spinal cord. Select embodiments of the implant incorporate one or more brakes including bores. And other preferred embodiments include superior and inferior plates having bores for receiving fasteners, such as screws.

An aspect of the present invention is to provide a generally wedge-shaped spinal surgical implant or brace.

Still another aspect of the present invention is to provide a spinal implant having a trapezoidal shaped platform or divider.

It is another aspect of the present invention to enable a method of implanting the generally trapezoidal shaped brace into a surgically created cavity of one or more vertebra.

Yet another aspect of the present invention is to provide a receptacle of an implant that after insertion into the surgically created cavity allows the surgical team to view the dura mater of the spinal cord through an opening of the receptacle.

Still another aspect of the present invention is to provide a receptacle of an implant that allows the packing of bone graft and/or osteogenic materials or substances through an opening facing the surgical team after the receptacle is inserted into the surgically created cavity.

It is still another aspect of the present invention to provide an implant having select embodiments that can be implanted through the patient's frontal or rearward side.

Yet still another aspect of the present invention is to provide a brace that includes a span of conjoined receptacles.

It is still another aspect of the present invention to provide an implant that includes a span of consecutively joined receptacles, where the span can be severed across a first cross-section or a first cross-section and a second cross-section to create a custom fitted implant for the surgically created cavity.

Still another aspect of the present invention is to provide an implant having a plurality of apertures.

It is another aspect of the present invention to provide an implant that includes one or brakes having bores for receiving fasteners such as bone screws.

Yet another aspect of the present invention is to provide an implant that includes upper and lower plates having one or more bores for receiving fasteners.

An embodiment of the present invention can be described as an implant capable of extending along an upright axis between an inferior side and a superior side of a surgically created cavity, wherein the implant is capable of implantation into the surgically created cavity and of affixture with bone, and wherein, prior to insertion into the cavity, the implant comprises: a span of consecutively joined receptacles into which osteogenic substances can be packed before completion of surgery; the span further comprising: a) one or more intermediate generally horizontal dividers, comprising: i) an inward short side; ii) a long side outward from and opposite of the short side; iii) a first converging side converging from a first end of the outward long side to a first end of the inward short side to create a first corner; iv) a second converging side converging from a second end of the outward long side to a second end of the inward short side to create a second corner; and v) a trapezoidal aperture created by inward edges of the short side, the long side, the first converging side and the second converging side; b) an inferior generally horizontal divider comprising an inferior aperture corresponding to the one or more trapezoidal apertures; c) a superior generally horizontal divider comprising a superior aperture corresponding to the one or more trapezoidal apertures; e) a first universal corner post contacting the one or more first corners and corresponding first corners of the inferior and the superior generally horizontally dividers; f) a second universal corner post contacting the one or more second corners and corresponding second corners of the inferior and the superior generally horizontally dividers; g) one or more first side upright universal posts positioned outward from the first corners and contacting the first corresponding sides of the one or more interior generally horizontal dividers, the inferior generally horizontal divider and the superior generally horizontal divider; h) one or more second side upright universal posts positioned outward from the second corners and contacting the second corresponding sides of the one or more interior generally horizontal dividers, the inferior generally horizontal divider and the superior generally horizontal divider, wherein combination of the interior generally horizontal dividers, the inferior generally horizontal divider, the superior generally horizontal divider, the universal corner posts and the upright universal posts creates openings of more than one cross-sectional area about the outer border of the implant, such that, prior to addition of osteogenic substances to the implant, a surgeon can see through the openings; i) a plurality of brakes integral with the long sides of the one or more interior generally horizontal dividers, wherein the brakes extend laterally beyond the first converging sides and the second converging sides of the one or more interior generally horizontal dividers, and wherein one or more of the brakes comprises a bore for receiving a fastener; j) a lower plate adjoining the long side of the inferior generally horizontal divider, wherein the lower plate comprises one or more bores; and k) an upper plate adjoining the long side of the superior generally horizontal divider, wherein the upper plate comprises one or more bores.

Another embodiment of the present invention can be described as an implant capable of fitting into a cavity surgically created between a superior vertebra and an inferior vertebra, the implant comprising: a) a trapezoidal base comprising: i) a short side; ii) a long side; iii) a first converging side creating a first corner with the short side and a third corner with the long side; iv) a second converging side creating a second corner with the short side and a fourth corner with the long side; and v) an aperture bounded by inner edges of the sides; b) a first corner post extending vertically from the first corner; c) a second corner post extending vertically from the second corner; d) a third corner post extending vertically from the third corner; e) a fourth corner post extending vertically from the fourth corner; f) a top attached to the vertical posts further comprising an opening corresponding to the base's aperture; g) one or more generally parallel dividers attached to the vertical posts; each generally parallel divider positioned between the base and the top, wherein the one or more generally parallel dividers, the base and the top form one or more receptacles capable of receiving osteogenic substances, and wherein, prior to addition of osteogenic substances into the one or more receptacles, arrangement of the one or more generally parallel dividers, the vertical posts, the base and the top includes openings allowing a surgeon to see through said implant; h) one or more first side brakes, comprising a bore, attached to the third post and extending laterally beyond an outer edge of the first converging side of the implant; i) one or more second side brakes, comprising a bore, attached to the fourth post and extending laterally beyond an outer edge of the second converging side of the implant; and j) a first plate, comprising a bore, attached to an outward edge of the base or an outward edge of the top.

Another embodiment of the present invention can be described as a length of consecutively joined receptacles comprising peripheral openings a surgeon can see through prior to addition of osteogenic substances, wherein the length of consecutively joined receptacles comprises: a) a generally vertical series of trapezoidal dividers, wherein each divider comprises: i) an inward side; ii) an outward side; iii) a first side connected with the outward side and the inward side forming a first outward corner with the outward side and a first inward corner with the inward side; iv) a second side connected with the outward side and the inward side forming a second outward corner with the outward side and a second inward corner with the inward side; and v) an aperture; b) a first universal corner post contacting the first inward corners; c) a second universal corner post contacting the second inward corners; d) one or more universal posts contacting the first sides of the dividers; and e) one or more universal posts contacting the second sides of the dividers; f) one or more first side brakes, comprising a bore, attached to the one or more first outward corners and extending laterally beyond the first sides; and g) one or more second side brakes, comprising a bore, attached to the one or more second outward corners and extending laterally beyond the second sides.

Another embodiment of the present invention can be described as an erect implant capable of implantation into a surgically cavity created between a superior vertebra and an inferior vertebra, comprising peripheral openings a surgeon can see through prior to addition of osteogenic substances, wherein the erect implant comprises: a) a series of trapezoidal dividers; b) a first universal corner post contacting first inward corners of the series; c) a second universal corner post contacting second inward corners of the series; d) one or more first universal posts contacting first sides of the series; e) one or more second universal posts contacting second sides of the series; f) one or more first side brakes attached to one or more outward edges of the series; the one or more first side brakes extending laterally beyond said first sides of the series, wherein at least one of the first side brakes comprises a bore for receiving a fastener; and g) one or more second side brakes attached to one or more outward edges of the series; the one or more second side brakes extending laterally beyond the second sides of the series, wherein at least one of the second side brakes comprises a bore for receiving a fastener.

Another embodiment of the present invention can be described as a generally vertical implant capable of implantation into a surgical cavity created between a superior vertebra and an inferior vertebra, comprising peripheral openings a surgeon can see through prior to addition of osteogenic substances, wherein the generally vertical implant comprises: a) a series of trapezoidal dividers; b) a first universal corner post contacting first inward corners of the series; c) a second universal corner post contacting second inward corners of the series; d) one or more first universal posts contacting first sides of the series; e) one or more second universal posts contacting second sides of the series; f) a first plate, comprising a bore, attached to an outward edge of a superior trapezoidal divider of the series; and g) a second plate, comprising a bore, attached to an outward edge of an inferior trapezoidal divider of the series.

It is the novel and unique interaction of these simple elements which creates the apparatus and methods, within the ambit of the present invention. Pursuant to Title 35 of the United States Code, descriptions of preferred embodiments follow. However, it is to be understood that the best mode descriptions do not limit the scope of the present invention.

BRIEF DESCRIPTION OF THE DRAWINGS

FIG. 15 is a frontal perspective of another embodiment of implant of the present invention.

FIG. 16 is a cross section of an embodiment of a plate of the present invention.

FIG. 17 is a frontal perspective of yet another embodiment of implant of the present invention.

FIG. 18 is a cross section of an embodiment of an outward side and inward edge of a superior or inferior divider of the present invention.

DESCRIPTION OF THE PREFERRED EMBODIMENTS

Figure 1:
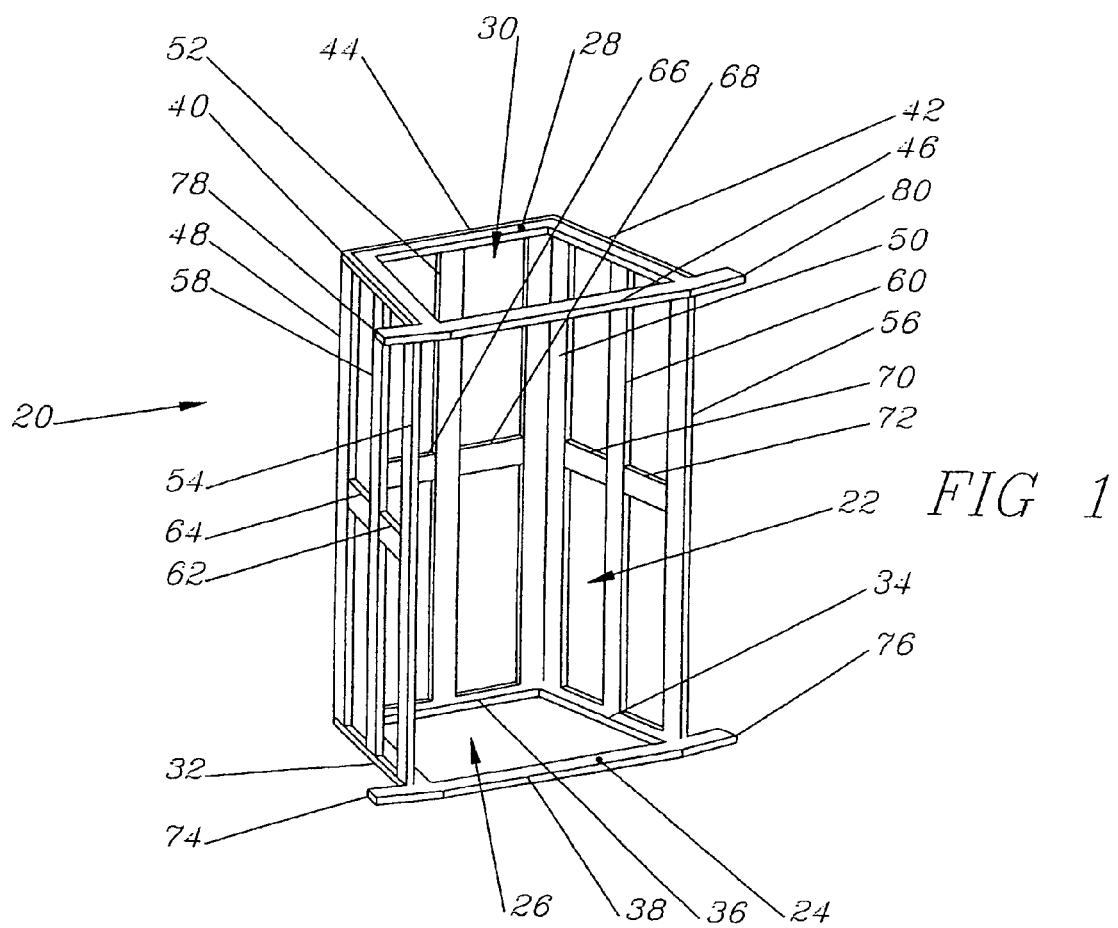
FIG. 1 is a frontal perspective of an embodiment of a receptacle of the present invention.

Although the disclosure hereof is detailed to enable those skilled in the art to practice the invention, the embodiments published herein merely exemplify the present invention.

In the most general sense, the present invention is a brace or implant that can be inserted into a cavity of the spinal column. Surgical removal of at least a part of one or more vertebra creates the cavity that will receive the implant. It has been discovered that many embodiments of the current implant can be useful for cervical spine surgeries and to can assist in stabilization of the postoperative spine. And many of the preferred embodiments of the present invention are particularly suited for corpectomy or partial corpectomy procedures.

After insertion of the brace into the cavity, the brace assists in stabilizing the spinal column against rotational movement and also resists the compression forces associated with gravitational forces on the spinal column. Select embodiments of the present invention can be implanted through the patient's frontal side, e.g., the frontal side of the patient's neck. Depending on the required surgical parameters, such as the length of the cavity and the number of vertebra involved in the procedure, the brace or implant can include a span of receptacles for receiving bone graft and/or other osteogenic substances. When a conjoined receptacle embodiment is practiced, the implant can be custom fitted to the desired size for the cavity into which the implant will be inserted. In one embodiment, the custom fitted implant can be created by severing through a cross-section of the brace, thereby creating two sections of the implant, including the one that is to be inserted into the cavity. In other embodiments, the custom fitted implant can be created by severing through a first cross-section and a second cross-section of the brace.

Preferred embodiments of the current spinal implant are generally trapezoidal in shape and are manufactured of titanium alloys, stainless steel, resorbable polymers or any other composition acceptable in the art. Within the scope of the present invention, it has advantageously been discovered that receptacles can have a height of approximately twelve millimeters, a width of from about six to about fifteen millimeters as measured along the narrowest parallel of the trapezoid and a depth of from about eight millimeters to about fifteen millimeters as measured along a converging side of the trapezoid. The size of implant to be inserted in the cavity is dependent upon the volume of the cavity. Prior to the surgical procedure, spans of braces of differing sizes can be provided to the surgical team—allowing the surgical team to select the appropriate volume and length for the implant to be inserted into the surgically created cavity. After a brace or implant has been inserted into the cavity, openings of the, receptacles into which bone graft, osteogenic and/or arthrodesis accelerating substances are packed can have areas from about 36 millimeters$^2$ to 225 millimeters$^2$ or greater.

Each receptacle of the present invention can be provided with corner posts or supports and other posts or supports that extend the height of the receptacle. Posts and corner posts are spaced about the outer border of the receptacle. One or more ties can extend crosswise between the posts and corner posts. Corner supports and the other supports are from about one millimeter to about two millimeters wide and are situated along the outer periphery of the receptacle in such a way as to create apertures between the posts and corner posts. Depending on the volume of the implant, the apertures between the corner posts and the other posts are from about one millimeter to about two millimeters wide.

Meeting a long felt but unfilled need in the spinal surgical arts, the unique structures of the present invention allow the surgical team to view the dura mater, before a receptacle is packed with bone graft, osteogenic and/or arthrodesis accelerating substances. Allowing the surgical team to view the dura mater while inserting the implant into the cavity reduces the possibility of having the brace inadvertently contact or injure the spinal cord. At the same time, the generally trapezoidally-shaped brace also assists the surgical team in not inserting the implant against the spinal cord. The contact between the cavity wall and the wedge-like brace can inhibit the implant from contacting the spinal cord. It appears that having the apertures of select embodiments in such close proximity with the cavity's walls increases the probability of the osteogenic materials procuring a blood supply. And it is believed that increasing the blood supply to the osteogenic materials held by a receptacle enhances local areas of arthrodesis between the vertebra and the bone graft. Select preferred embodiments of the present invention are also provided with brakes to further impede the implant from contacting the spinal column.

FIG. 1 is a frontal perspective of an embodiment of a receptacle of the present invention. When implanted into a surgically created cavity of the spinal column, opening (22) of receptacle or brace (20) will face the surgical team. A first trapezoidal platform (24) includes aperture (26) and a second trapezoidal platform (28) includes aperture (30). First platform (24) includes first converging side (32), second converging side (34), shorter side (36) and longer side (38). Second platform (28) is provided with first converging side (40), second converging side (42), shorter side (44) and longer side (46). Platform (24) is spaced apart from platform (28), and corner posts (48) and (50) extend between first platform (24) and second platform (28). Intermediate of first corner post (48) and second corner post (50) is frontal post (52). Proximate longer side (38) of platform (24) and longer side (46) of platform (28) and extending between platform (24) and platform (28) are posts (54) and (56).

Although not required to practice the present invention, as shown in FIG. 1, in select preferred embodiments, positioned between corner post or support (48) and post or support (54) is post or support (58) that extends between first converging side (32) of platform (24) and first converging side of (40) of platform (28). In a similar manner, post or support (60) is positioned between corner post or support (50) and post or support (56) and extends between second converging side (34) of platform (24) and second converging side of (42) of platform (28). Select preferred embodiments can include one or more ties extending between or connecting the posts or supports.

By way of illustration, as shown in FIG. 1, tie (62) connects post (54) and post (58), tie (64) connects post (58) and post (48), tie (66) connects post (48) and post (52), tie (68) connects post (52) and post (50), tie (70) connects post (50) and post (60) and tie (72) connects post (60) and post (56). When surgical parameters mandate, one or more ties can be eliminated from brace (20). In an alternate preferred embodiment, a first tie can connect all posts positioned along the first converging side (32, 40) of implant (20), a second tie can connect all posts located near the frontal plane of brace (20) and a third tie can connect all posts positioned along the second converging side (34, 42) of receptacle (20).

When surgical parameters dictate, more than three or less than three posts can be positioned along either the first converging side, the second converging side or both of implant (20). In an alternate preferred embodiment, frontal post (52) can be eliminated. And in select preferred embodiments, instead of a plurality of ties interconnecting with the various posts, a single tie can interconnect posts (48), (50), (52), (54), (56), (58) and (60).

With reference still to FIG. 1, brake (74) extends laterally of first converging side of platform (24) and brake (76) extends laterally of second converging side of platform (24). Brake (78) extends laterally of first converging side of platform (28) and brake (80) extends laterally of second converging side of platform (28). Depending upon preselected parameters, for an embodiment employing brakes, a receptacle can be provided with one or more brakes.

Figure 2:
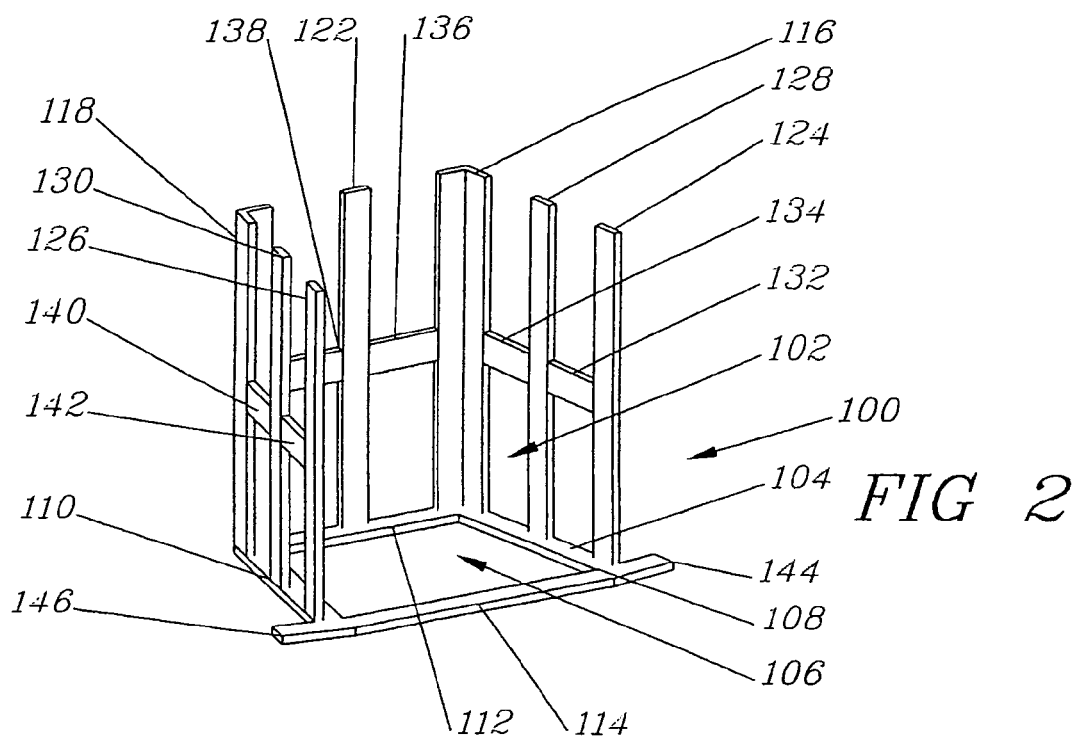
FIG. 2 is a frontal perspective of another embodiment of a receptacle of the present invention.

FIG. 2 is a frontal perspective of another embodiment of a receptacle of the present invention. When implanted into a surgically created cavity of the spinal column, opening (102) of receptacle or brace (100) will face the surgical team. Trapezoidal platform (104) includes aperture (106), first converging side (108), second converging side (110), shorter side (112) and longer side (114). First corner spike (116) and second corner spike (118) extend from shorter side (112) of platform (104). Seventh spike (122) is intermediate first corner spike (116) and second corner spike (118). Third spike (124) and fifth spike (128) extend from first converging side (108). Fourth spike (126) and sixth spike (130) extend from second converging side (110) of platform (104). As shown in FIG. 2, seven spikes are strategically extended from platform (104). However, when surgical parameters mandate, more or less than seven spikes can be extended from platform (104).

Select preferred embodiments can include one or more ties extending between or connecting the spikes. By way of illustration, as shown in FIG. 2, tie (132) connects spike (124) and spike (128), tie (134) connects spike (128) and spike (116), tie (136) connects spike (116) and spike (122), tie (138) connects spike (122) and spike (118), tie (140) connects spike (118) and spike (130) and tie (142) connects spike (130) and spike (126). When surgical parameters mandate, one or more ties can be eliminated from brace (100). In an alternate preferred embodiment, a first tie can connect all spikes positioned along the first converging side (108) of implant (100), a second tie can connect all spikes extending from shorter side (112) of brace (100) and a third tie can connect all spikes positioned along the second converging side (110) of receptacle (100). In select preferred embodiments, instead of a plurality of ties interconnecting with the various spikes, a single tie can interconnect spikes (116), (118), (122), (124), (126), (128) and (130). ii Brake (144) extends laterally of first converging side (108) of platform (104) and brake (146) extends laterally of second converging side (110) of platform (104).

Figure 3:
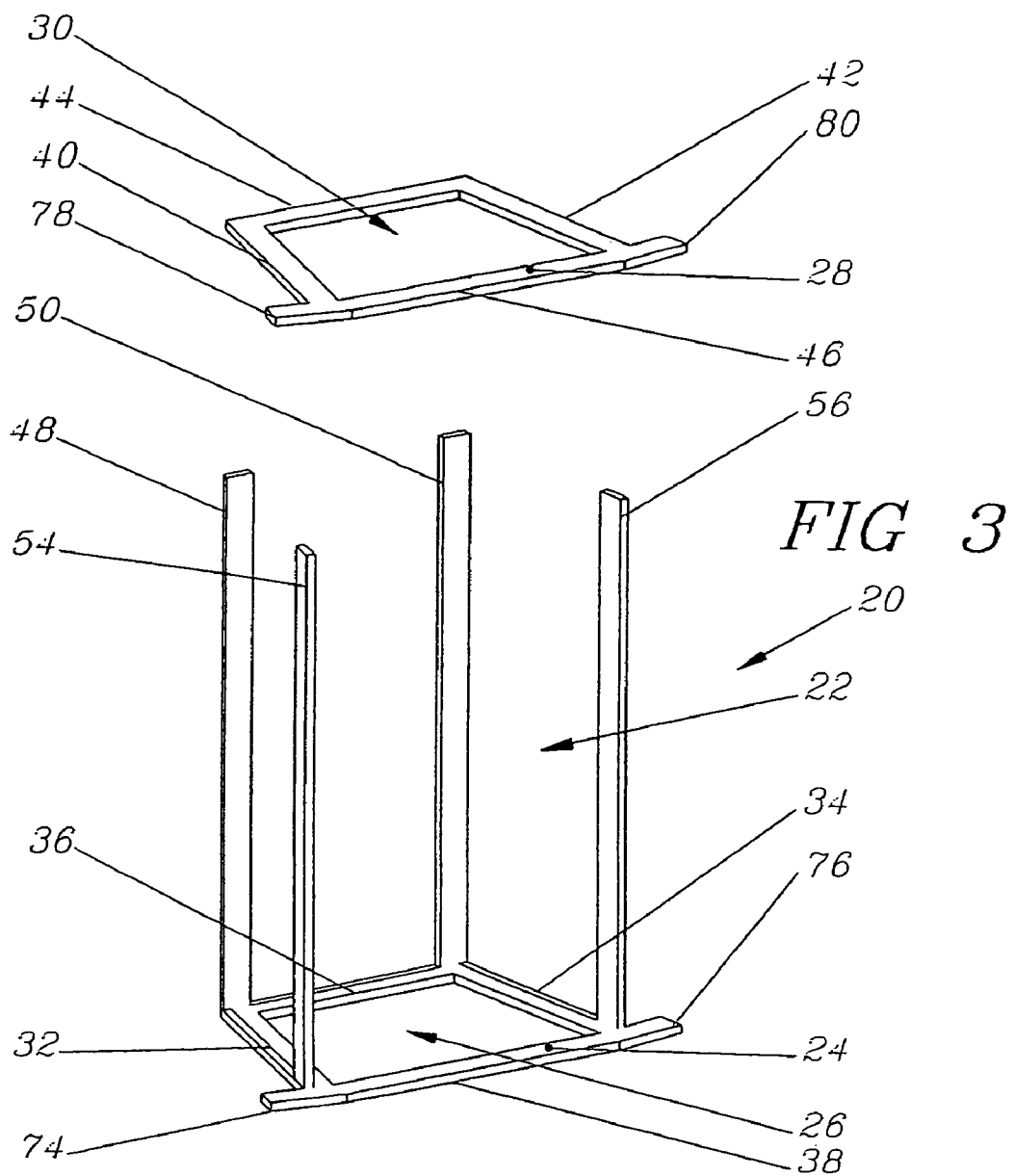
FIG. 3 is an exploded view of another embodiment of the present invention that does not utilize ties.

FIG. 3 is an exploded view of another embodiment of the present invention. When implanted into a surgically created cavity of the spinal column, opening (22) of receptacle or brace (20) will face the surgical team. A first trapezoidal platform (24) includes aperture (26) and a second trapezoidal platform (28) includes aperture (30). First platform (24) includes first converging side (32), second converging side (34), shorter side (36) and longer side (38). Second platform (28) is provided with first converging side (40), second converging side (42), shorter side (44) and longer side (46). When connected to receptacle (20), platform (28) is spaced apart from platform (24). Corner supports or posts (48) and (50) extend from first platform (24). Positioned proximate longer side (38) and extending from platform (24) are support (54) and support (56). Although not shown in FIG. 3, select preferred embodiments can include one or more ties extending between or connecting the supports. Brakes (74), (76), (78) and (80) extend laterally from the converging sides of platforms (24) and (28).

Figure 4:
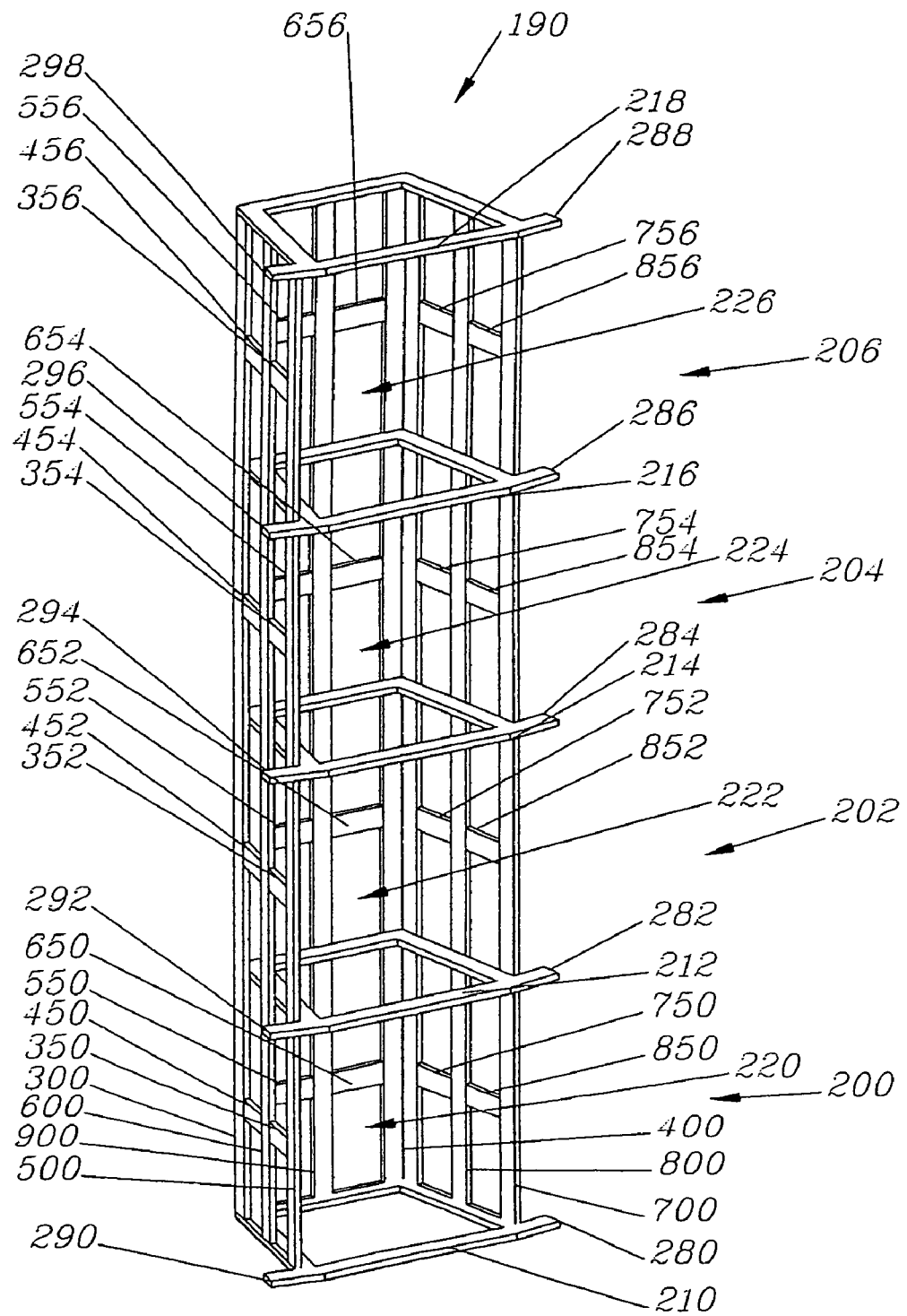
FIG. 4 is a frontal view of a span of consecutively joined receptacles.

FIG. 4 is a frontal view of span (190) of consecutively joined receptacles. As shown, by way of illustration rather than limitation, as to the number of receptacles, supports, ties or brakes, span (190) includes receptacles (200), (202), (204) and (206). Receptacle (200) includes dividers (210) and (212); receptacle (202) includes dividers (212) and (214); receptacle (204) includes dividers (214) and (216); and receptacle (206) includes dividers (216) and (218). Each divider (210, 212, 214, 216, 218) is provided with a shorter side, a longer side, a first converging side and a second converging side. Receptacles (200, 202, 204 and 206) have openings (220, 222, 224 and 226), respectively. The openings allow the surgical team to view the dura mater before one or more receptacles is packed with osteogenic substances or materials.

Receptacles (200) and (206) are end receptacles of span (190). Receptacles (202) and (204) are conjoined receptacles of span (190). Corner support (300) extends between divider (210) and divider (218) and corner support (400) extends between divider (210) and divider (218). First converging side of span (190) includes first support (500) and second support (600) extending between divider (210) and divider (218) second converging side of span (190) includes third support (700) and fourth support (800) extending between divider (210) and divider (218). Intermediate support (900) extends between divider (210) and divider (218).

With reference to receptacle (200), tie (350) connects first support (500) and second support (600); tie (450) connects second support (600) and corner support (300); tie (550) connects corner support (300) and intermediate support (900); tie (650) connects intermediate support (900) and corner support (400); tie (750) connects corner support (400) and fourth support (800); and tie (850) connects fourth support (800) and third support (700). With reference to receptacle (202), tie (352) connects first support (500) and second support (600); tie (452) connects second support (600) and corner support (300); tie (552) connects corner support (300) and intermediate support (900); tie (652) connects intermediate support (900) and corner support (400); tie (752) connects corner support (400) and fourth support (800); and tie (852) connects fourth support (800) and third support (700). With reference to receptacle (204), tie (354) connects first support (500) and second support (600); tie (454) connects second support (600) and corner support (300); tie (554) connects corner support (300) and intermediate support (900); tie (654) connects intermediate support (900) and corner support (400); tie (754) connects corner support (400) and fourth support (800); and tie (854) connects fourth support (800) and third support (700). With reference to receptacle (206), tie (356) connects first support (500) and second support (600); tie (456) connects second support (600) and corner support (300); tie (556) connects corner support (300) and intermediate support (900); tie (656) connects intermediate support (900) and corner support (400); tie (756) connects corner support (400) and fourth support (800); and tie (856) connects fourth support (800) and third support (700).

Divider (210) is provided with brakes (280) and (290); divider (212) is provided with brakes (282) and (292); divider (214) is provided with brakes (284) and (294); divider (216) is provided with brakes (286) and (296); and divider (218) is provided with brakes (288) and (298). As shown in the FIG. 4 embodiment, dividers (210 and 218) adjoin supports (300, 400, 500, 600, 700, 800 and 900), whereas dividers (212, 214 and 216) are positioned inwardly from supports (300, 400, 500, 600, 700, 800 and 900). However, depending on engineering parameters, other embodiments can include spans where each divider is flush with the supports, spans where each divider is positioned inwardly from the supports or spans where the supports are positioned inwardly from the dividers.

Figure 5:
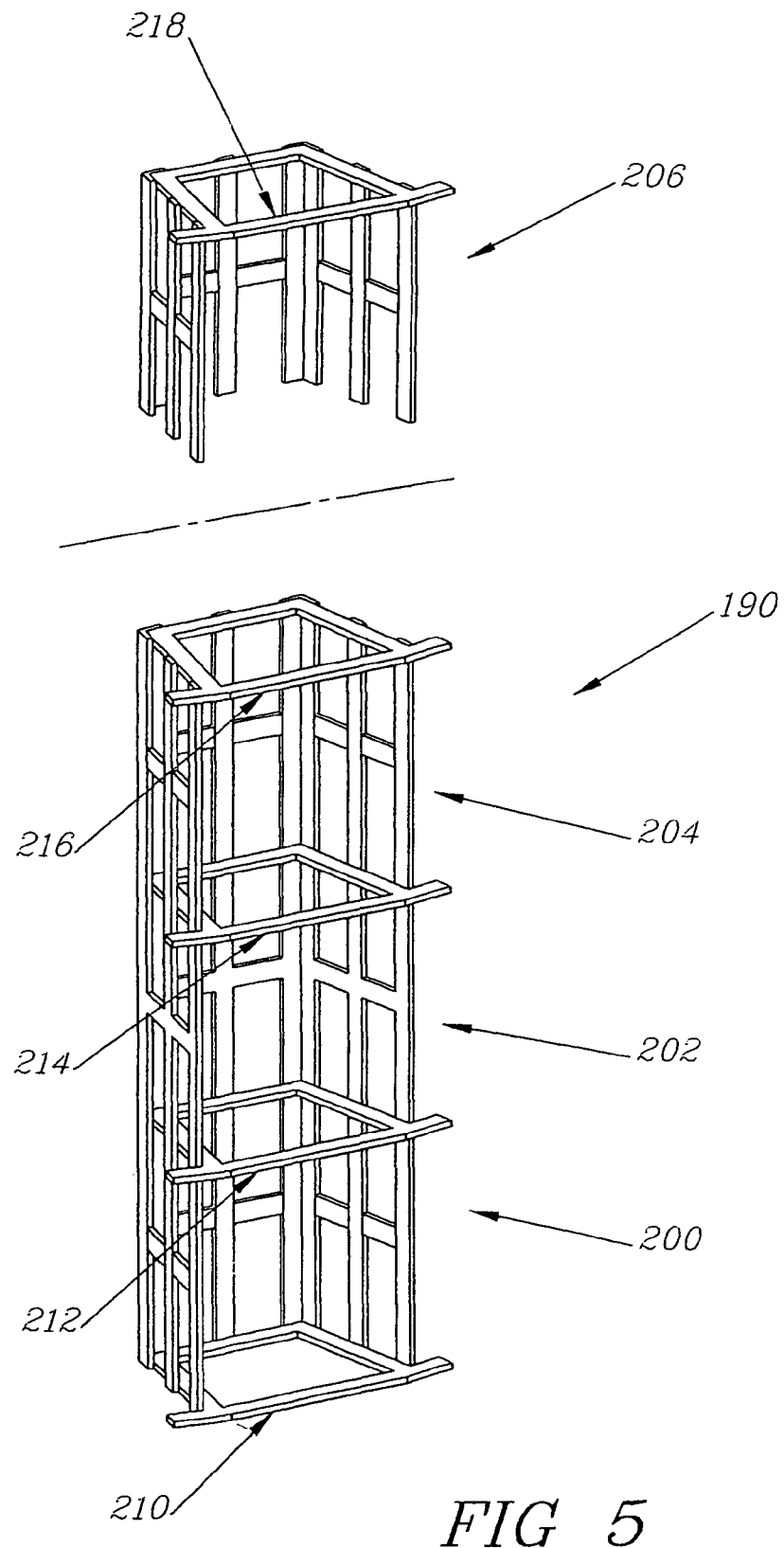
FIG. 5 is an exploded view of the invention of FIG. 4 where span (190) has been severed along a first cross-section to separate receptacle (206) away from span (190)—leaving an implant with a generally trapezoidal shaped platform or divider (210) at a first end of the implant and a generally trapezoidal shaped platform or divider (216) at a second end of the implant.

FIG. 5 is an exploded view of span (190) that has been severed along a first cross-section to separate receptacle (206) away from the remainder of span (190) and receptacles (200, 202 and 204)—leaving an implant with a generally trapezoidal shaped platform or divider (210) at a first end of the implant and a generally trapezoidal shaped platform or divider (216) at a second end of the implant. As shown in FIG. 5, each divider is positioned inwardly of the supports.

Figure 6:
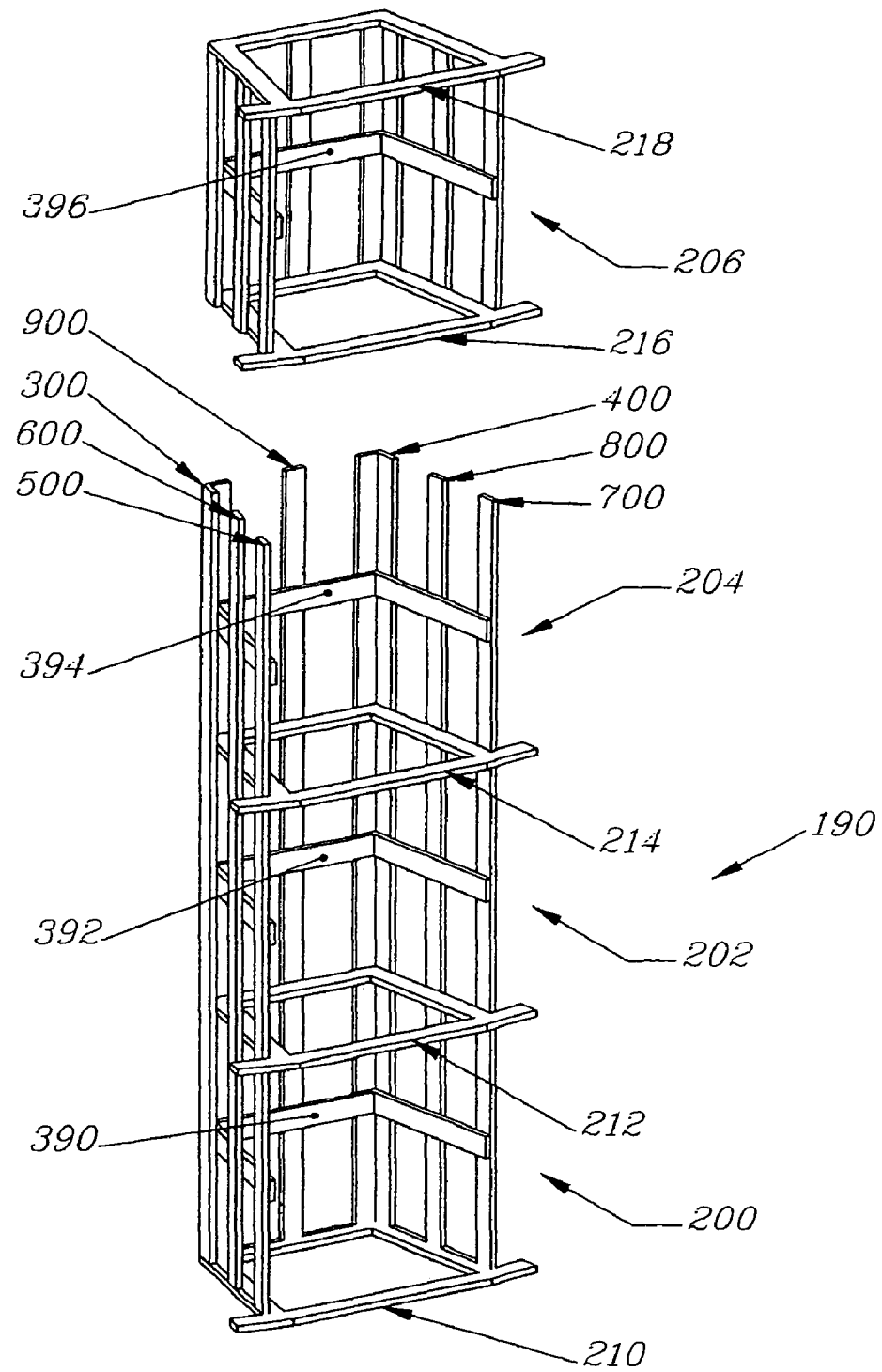
FIG. 6 is an exploded view of the invention of FIG. 4 where span (190) has been severed along a first cross-section to create an implant with a generally trapezoidal shaped divider (210) at a first end of the implant and supports or spikes (304, 404, 504, 604, 704, 804 and 904) exposed at the opposite and second end of span (190).

FIG. 6 is an exploded view of an embodiment similar to the invention of FIG. 4. Rather than a plurality of ties for receptacles (200), (202), (204) and (206), a single tie is incorporated into each receptacle. Tie (390) reinforces receptacle (200); tie (392) reinforces receptacle (202); tie (394) reinforces receptacle (204) and tie (396) reinforces receptacle (206). As shown in FIG. 6, span (190) has been severed along a first cross-section to create an implant with a generally trapezoidal shaped divider (210) at a first end of the implant and supports or spikes (300, 400, 500, 600, 700, 800 and 900) exposed at the opposite and second end of span (190).

Figure 7:
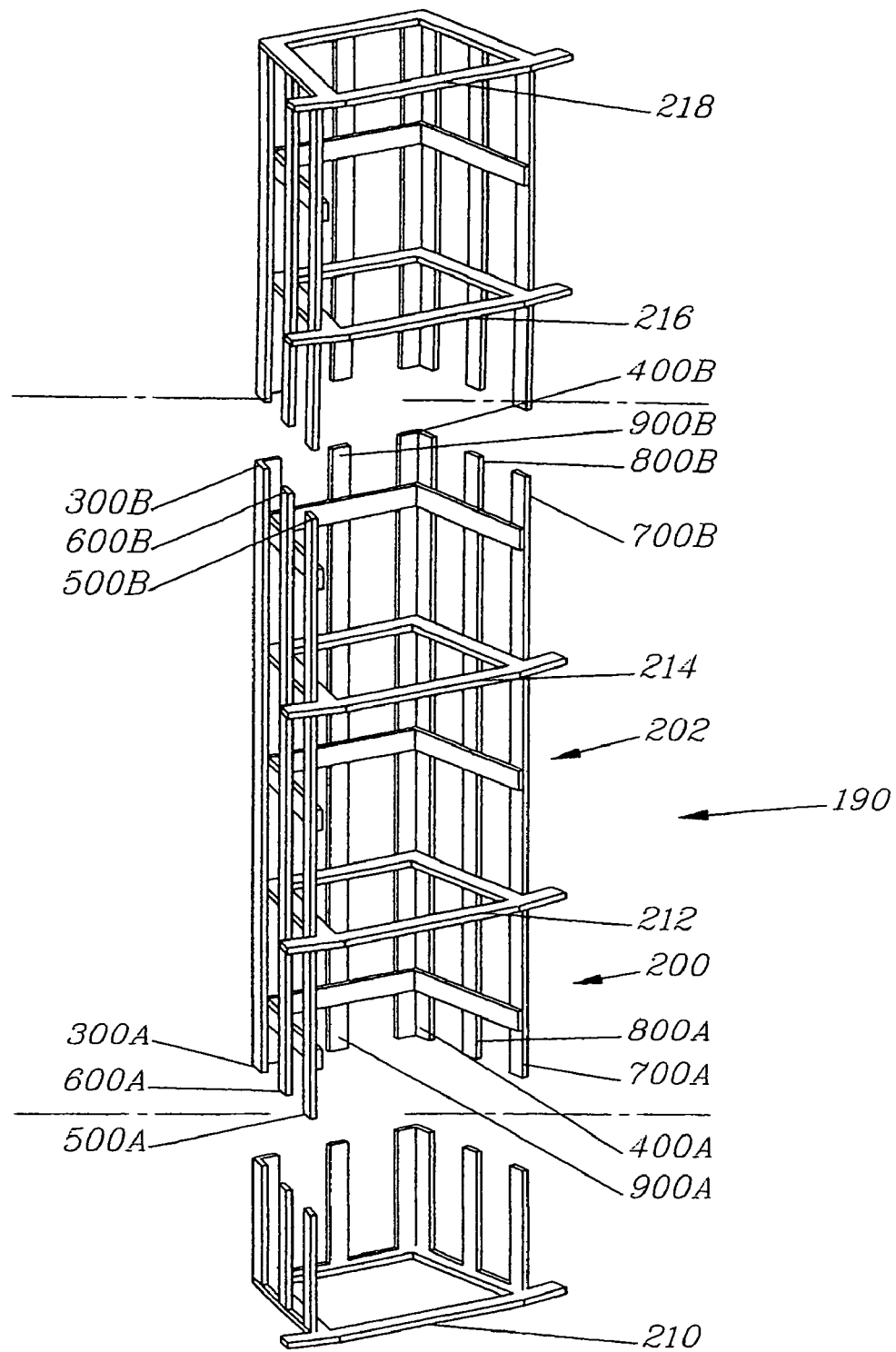
FIG. 7 is an exploded view of the invention of FIG. 4 where span (190) has been severed along a first cross-section and a second cross-section to create an implant with supports or spikes (300, 400, 500, 600, 700, 800 and 900) at first end of the implant and supports or spikes (304, 404, 504, 604, 704, 804 and 904) exposed at the opposite and second end of span (190).

FIG. 7 is an exploded view of the invention of FIG. 6 where span (190) has been severed along a first cross-section and a second cross-section to create an implant with supports or spikes (300A, 400A, 500A, 600A, 700A, 800A and 900A) at first end of the implant and supports or spikes (300B, 400B, 500B, 600B, 700B, 800B and 900B) exposed at the opposite and second end of span (190).

Figure 8:
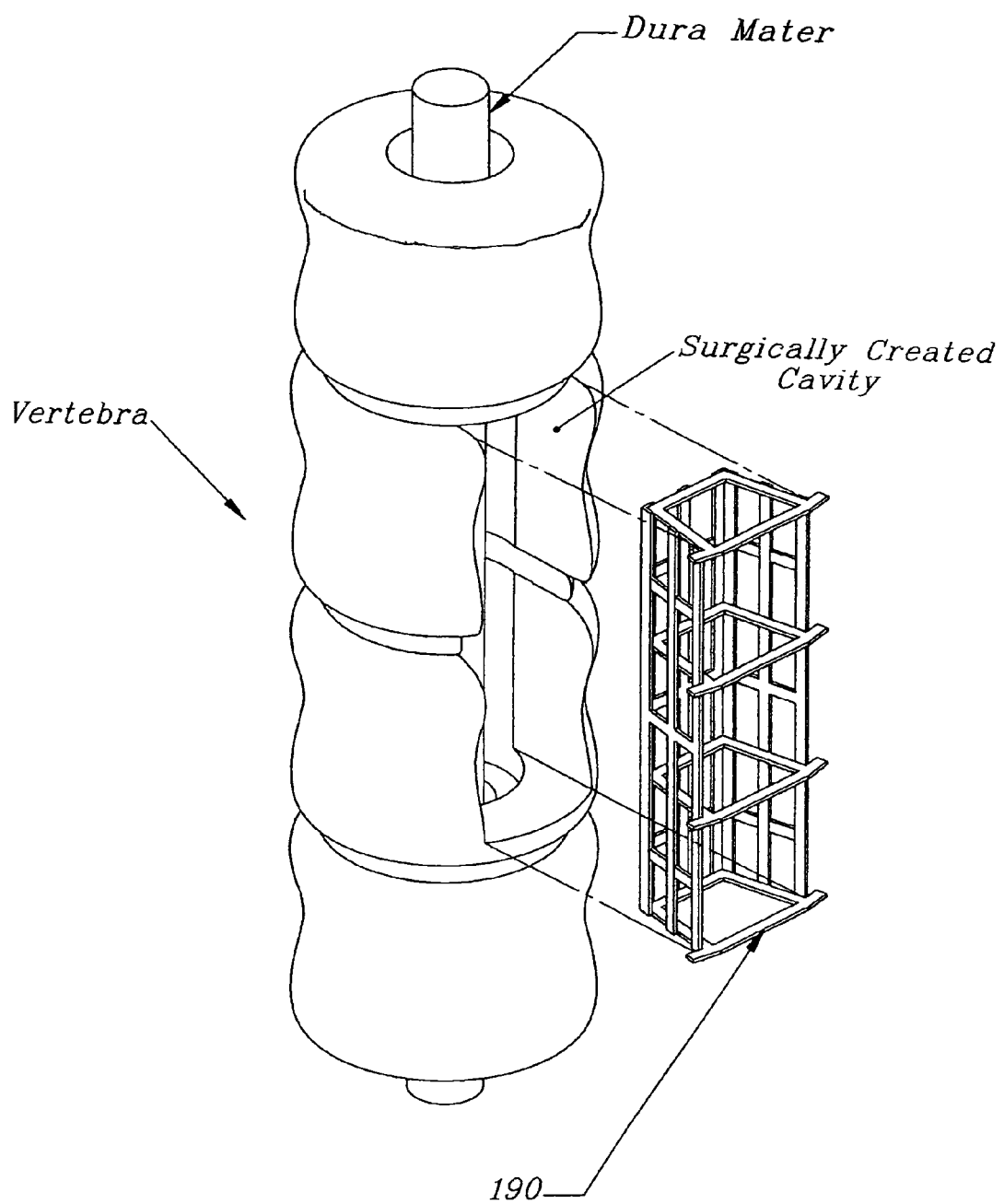
FIG. 8 is a perspective of a surgically created cavity in a vertebra and an embodiment of the present invention.
Figure 9:
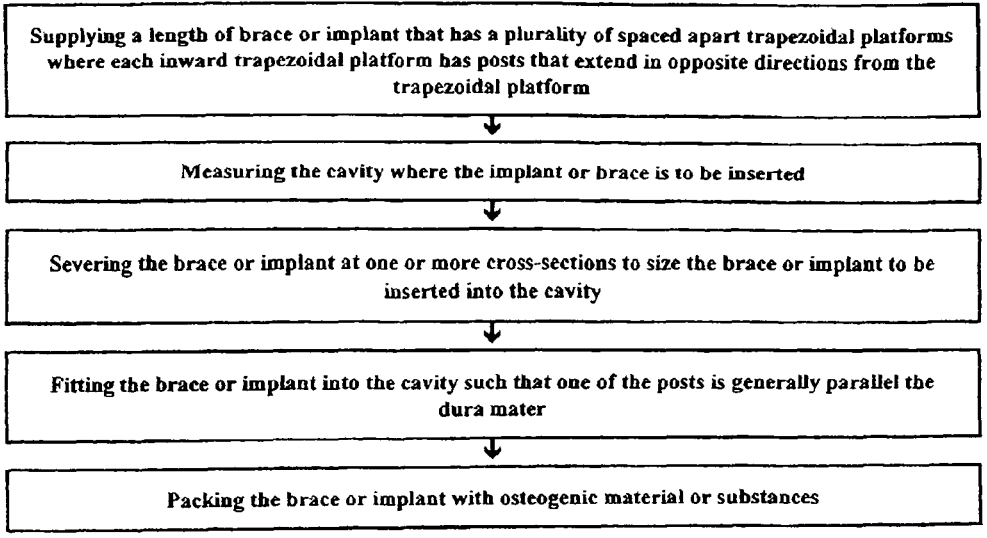
FIG. 9 is an exemplification of the steps of an embodiment of the current method.
Figure 10:
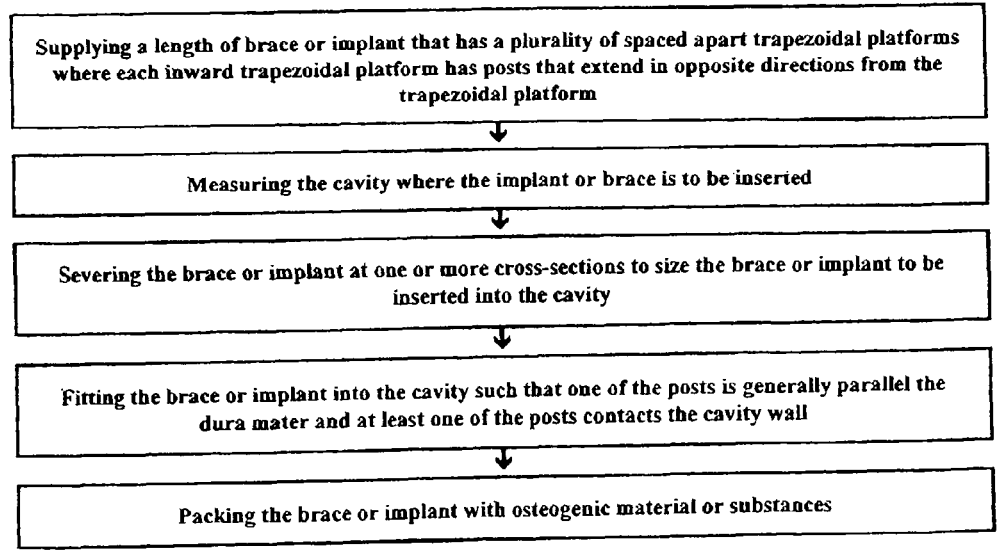
FIG. 10 is a diagrammatic representation of the steps of another embodiment of the present invention.
Figure 11:
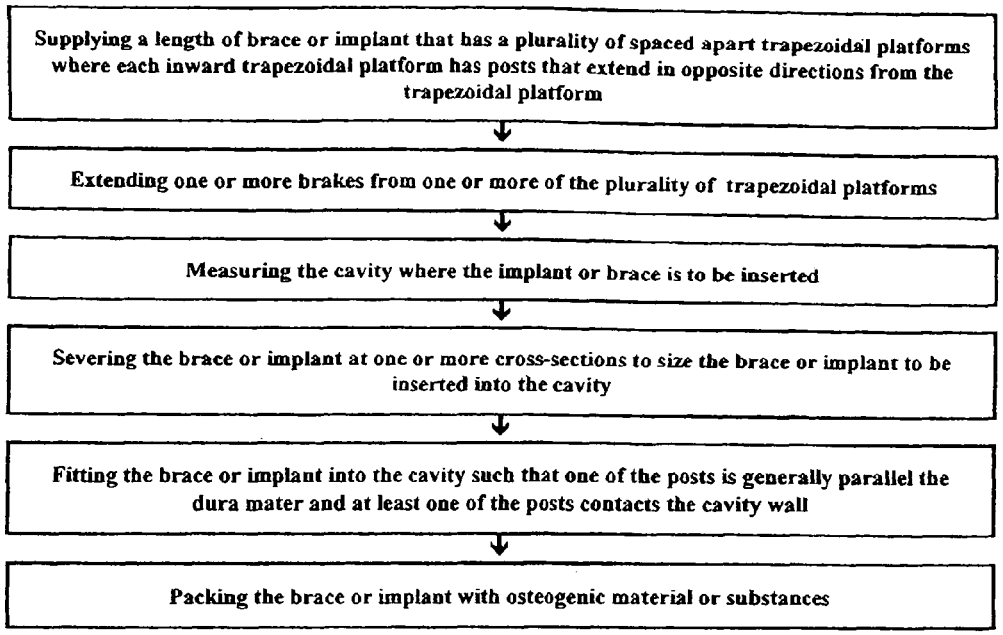
FIG. 11 is another diagrammatic representation of the steps of still another embodiment of the present invention.
Figure 12:
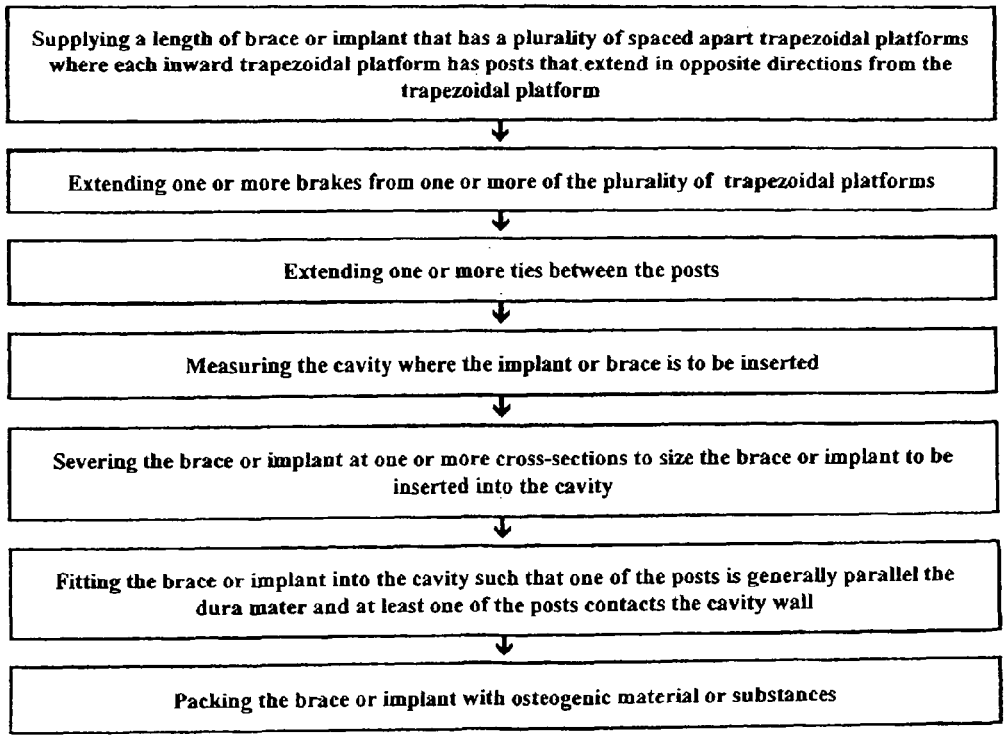
FIG. 12 is yet another exemplification of the steps of yet another embodiment of the present invention.

FIG. 8 portrays an embodiment of a span (190) of the present invention that can be inserted into a surgically created cavity of a vertebra.

Steps associated with the practice of the methods of embodiments the present invention are set forth in FIGS. 9-12. Those steps are related to the practice of using the spinal implant structures previously set forth. Moreover, the majority of the preferred embodiments of the present invention practice the packing of osteogenic materials or substances into the implant's receptacle after the brace has been inserted into the cavity. Importantly, preferred methods of the current invention can be used to create implants that have a trapezoidal platform at each end of the implant, a trapezoidal platform at the first end of the brace and a set of spikes corresponding to the posts at the second end of the implant or a set of spikes at each end of the implant.

Figure 13:
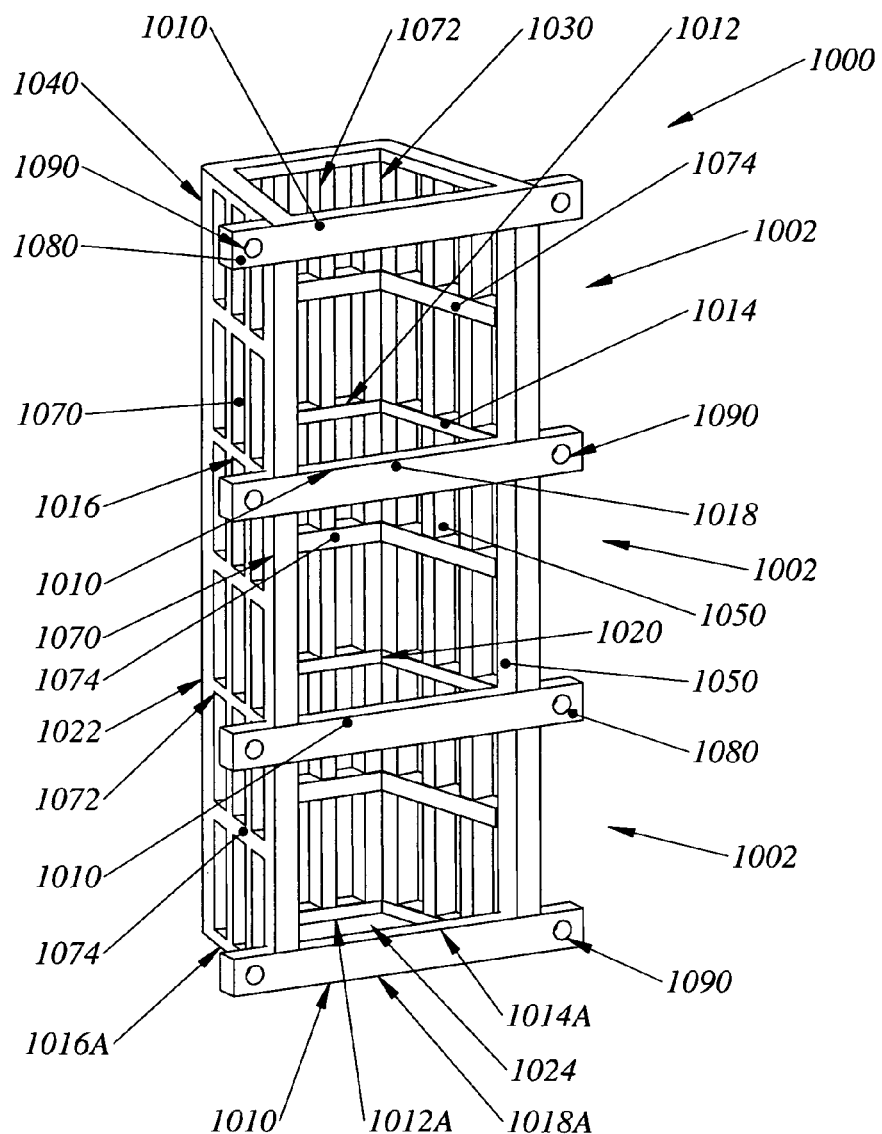
FIG. 13 is a frontal perspective of an embodiment of implant of the present invention.

FIG. 13 portrays a span (1000) of receptacles (1002) that can be packed with osteogenic materials prior to the completion of spinal surgery. Span (1000) is manufactured of titanium, stainless steel, resorbable polymers, non-resorbable polymers or combinations thereof. By way of illustration, generally horizontal divider (1010) has inward side (1012) (after insertion into the surgically created cavity, positioned near the dura mater of the spinal cord), long outward side (1018), first converging side (1014) and second converging side (1016). As shown, span (1000) includes a plurality of dividers (1010), including intermediate or interior, superior and inferior dividers (1010). Superior divider (1010) can function as a top of span (1000) while inferior divider (1010) can function as a base of implant (1000). Intersection of first converging side (1014) and short side (1012) creates first corner (1020) and intersection of inward side (1012) and second converging side (1016) creates second corner (1022), such that each divider (1010) has first corner (1020) and second corner (1022). In select embodiments, inward edges (1012A, 1014A, 1016A and 1018A) of inward side (1012), long side (1018), first converging side (1014) and second converging side (1016) create generally trapezoidal aperture (1024), while in other embodiments, inward edges are constructed to create an aperture of other than trapezoidal dimensions. First universal corner post (1030) contacts first corners (1020) and second universal corner post (1040) contacts second corners (1022). In the embodiment disclosed in FIG. 13, first universal corner post (1030) is angled at about ninety degrees to simultaneously connect with inward side (1012) and first converging side (1014) and second universal corner post (1040) is angled at about ninety degrees to simultaneously connect with inward side (1012) and second converging side (1016).

In select embodiments, one or more first side universal posts (1050) can contact first converging sides of dividers (1010) of span (1000) while one or more second side universal posts (1070) can contact second converging sides of dividers (1010) of span (1000). One of the first side universal posts (1050) can function as a third corner post and one of the second side universal posts (1070) can function as a fourth corner post. In other embodiments, one or more inward universal posts (1072) can contact short sides of dividers (1010). Implant (1000) can also include one or more ties (1074) contacting universal corner posts (1030, 1040) and universal posts (1050, 1070, 1072). Most preferably, ties (1074) are positioned on the inward sides of the universal posts.

As shown in FIG. 13, the combination of the interior generally horizontal dividers, the inferior generally horizontal divider, the superior generally horizontal divider, the universal corner posts (1030, 1040) and the universal posts (1050, 1070, 1072) contacting the first and second converging sides of span (1000) creates openings of more than one cross-sectional area about the outer border of the span or implant (1000)—allowing the surgeon to see through the openings, prior to the addition of osteogenic substances into implant (1000).

In the FIG. 13 embodiment, implant (1000) is provided with a plurality of brakes (1080) integral with one or more long outward sides (1018) of generally horizontal dividers (1010). However, in other embodiments of current invention, brakes (1080) need not be integral with outward sides (1018) of generally horizontal dividers (1010), and brakes (1080) can be affixed with outward universal posts (1050, 1070). One or more brakes (1080) are provided with bore (1090). Brakes (1080) extend laterally beyond first converging sides and second converging sides of dividers (1010) of implant (1000). Brakes (1080) assist the surgeon in minimizing potential damage to the spinal cord from over-insertion of the implant into the surgically created cavity.

Figure 14:
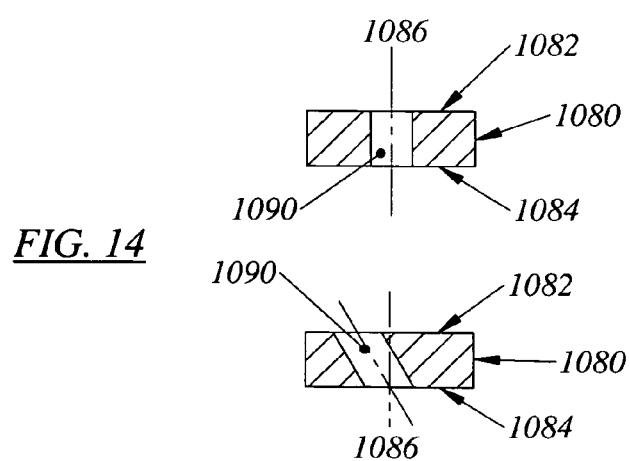
FIG. 14 is a cross section of an embodiment of a brake of the present invention.

Depending on predetermined engineering parameters, as shown in FIG. 14, brake (1080) can include bore (1090) that is perpendicular to outward side (1082) and inward side (1084) of brake (1090) or brake (1080) can include bore (1090) that is angled at other than perpendicular from the outward side (1082) and inward side (1084) of brake (1080). It has been discovered that bore (1090) can be angled from about 1 degree to about 60 degrees away from the bore's reference axis (1086), where the reference axis (1086) equates to the perpendicular axis between outward side (1082) and inward side (1084) of brake (1080).

In select preferred embodiments, bores (1090) of brakes (1080) associated with superior generally horizontal divider (1010) as well as the bores (1090) of brakes (1080) associated with generally horizontal dividers (1010) in proximity with superior divider (1010) are angled upward from outward side (1082) through inward side (1084) of brake (1080) and bores (1090) of brakes (1080) associated with inferior generally horizontal divider (1010) as well as the bores (1090) of brakes (1080) associated with generally horizontal dividers (1010) in proximity with inferior divider (1010) are angled downward from outward side (1082) through inward side (1084) of brake (1080). Bores (1090) function to receive a fastener, such as a screw (not shown in this view) that assists in securing the implant to bone.

Turning to the embodiment disclosed in FIG. 15, implant (1000) is provided with a superior plate (1100) attached to outward side (1018) of an upper or superior divider (1010). In similar fashion, inferior plate (1200) is attached to outward side (1018) of a lower or inferior divider (1010). Upper plate (1100) has two bores (1102) for receiving fasteners to assist in securing implant (1000) to bone. Lower plate (1200) includes two bores (1202) for receiving fasteners that assist in securing span (1000) to bone. Although upper plate (1100) and lower plate (1200) are shown with a plurality of bores, Applicant's current invention can function when upper plate (1100) and lower plate (1200), each include only a single bore (1102, 1202).

As shown in the embodiment of FIG. 15, superior plate (1100) extends upward from superior divider (1010) and inferior plate (1200) depends downward from inferior divider (1010). In select embodiments, superior plate (1100) extends upward in a plane perpendicular to outward side (1018) of upper divider (1010) and inferior plate (1200) depends downward in a plane perpendicular to outward side (1018) of lower divider (1010). Intermediate dividers (1010) include one or more brakes (1080) having bore (1090). Brakes (1080) extend laterally beyond first converging sides and second converging sides of dividers (1010) of implant (1000).

With reference to FIG. 16, plate (1100) can include one or more bores (1102) where each bore (1102) is perpendicular to outward side (1104) and inward side (1106) of plate (1100) or plate (1100) can include one or more bores (1102) that are angled at other than perpendicular from the outward side (1104) and inward side (1106) of plate (1100). By way of example, bores (1102) can be angled from about 1 degree to about 60 degrees away from the bore's reference axis (1110), where the reference axis (1110) equates to the perpendicular axis between outward side (1104) and inward side (1106) of plate (1000). Plate (1200) and one or more bores (1202) are manufactured in a similar fashion to plate (1100) and one or more bores (1102).

In select preferred embodiments, bores (1102) of plate (1100) are angled upward from outward side (1104) through inward side (1106) of plate (1100) and bores (1202) of plate (1200) are angled downward from the outward side of plate (1200) through the inward side of plate (1200) One or more bores (1102, 1202) function to receive a fastener, such as a screw (not shown in this view) that assists in securing the implant to bone. Unlike the FIG. 13 embodiment, brakes (1080) and bores (1090) of the FIG. 15 embodiment are not integral with outward sides (1018) of dividers (1010). Bores (1090) of brakes (1080) in proximity with superior plate (1100) can be angled upward while bores (1090) of brakes in proximity with inferior plate (1200) can be angled downward.

With reference to an embodiment portrayed in FIG. 17, implant (1000) is provided with superior divider (1010) that includes a plurality of bores (1092) integral with outward side (1018) and inward edge (1018A) of superior divider (1010) and inferior divider (1010) includes a plurality of bores (1092) integral with outward side (1018) and inward edge (1018A) of inferior divider (1010). Bores (1092) are inset from first converging sides (1014) and second converging sides (1016) of dividers (1010) of implant (1000). As depicted in FIG. 18, superior divider (1010) includes one or more bores (1092) where each bore (1092) is angled at other than perpendicular from the outward side (1018) and inward edge (1018) of divider (1010). Bores (1092) can be angled from about 1 degree to about 60 degrees away from the bore's reference axis (1096), where the reference axis (1096) equates to the perpendicular axis between outward side (1018) and inward edge (1018A) of divider (1010). Inferior divider (1010) and one or more bores (1092) are manufactured in a similar fashion to superior (1010) and one or more bores (1010).

In the preferred embodiments, bores (1092) of superior divider (1010) are angled upward from outward side (1018) through inward edge (1018A) of superior divider (1010) and bores (1092) of inferior divider (1010) are angled downward from the outward side (1018) through inward edge (1018A) of inferior divider (1010). Bores (1092) function to receive a fastener, such as a screw (not shown in this view) that assists in securing the implant to bone. Brakes (1080) and bores (1090) of the FIG. 17 embodiment are identical to brakes (1080) and bores (1090) of the FIG. 13 embodiment. Bores (1090) of brakes (1080) in proximity with superior divider (1010) can be angled upward while bores (1090) of brakes (1080) in proximity with inferior divider (1010) can be angled downward.

Having disclosed the invention as required by Title 35 of the United States Code, Applicant now prays respectfully that Letters Patent be granted for his invention in accordance with the scope of the claims appended hereto.

What is claimed is:

1. An implant capable of extending along an upright axis between an inferior side and a superior side of a surgically created cavity, wherein said implant is capable of implantation into said surgically created cavity and of affixture with bone, and wherein, prior to insertion into said cavity, said implant comprises: a span of consecutively joined receptacles into which osteogenic substances can be packed before completion of surgery; said span further comprising:
   a) titanium, stainless steel, resorbable polymers, non-resorbable polymers or combinations thereof;
   b) one or more intermediate generally horizontal dividers, comprising:
      i) an inward short side;
      ii) a long side outward from and opposite of said short side;
      iii) a first converging side converging from a first end of said outward long side to a first end of said inward short side to create a first corner;
      iv) a second converging side converging from a second end of said outward long side to a second end of said inward short side to create a second corner; and
      v) a trapezoidal aperture created by inward edges of said short side, said long side, said first converging side and said second converging side;

c) an inferior generally horizontal divider comprising an inferior aperture corresponding to said one or more trapezoidal apertures;
d) a superior generally horizontal divider comprising a superior aperture corresponding to said one or more trapezoidal apertures;
e) a first universal corner post contacting said one or more first corners and corresponding first corners of said inferior and said superior generally horizontally dividers;
f) a second universal corner post contacting said one or more second corners and corresponding second corners of said inferior and said superior generally horizontally dividers;
g) one or more first side upright universal posts positioned outward from said first corners and contacting said first corresponding sides of said one or more interior generally horizontal dividers, said inferior generally horizontal divider and said superior generally horizontal divider;
h) one or more second side upright universal posts positioned outward from said second corners and contacting said second corresponding sides of said one or more interior generally horizontal dividers, said inferior generally horizontal divider and said superior generally horizontal divider, wherein combination of said interior generally horizontal dividers, said inferior generally horizontal divider, said superior generally horizontal divider, said universal corner posts and said upright universal posts creates openings of more than one cross-sectional area about the outer border of said implant, such that, prior to addition of osteogenic substances to said implant, a surgeon can see through said openings;
i) a plurality of brakes integral with said long sides of said one or more interior generally horizontal dividers, wherein said brakes extend laterally beyond said first converging sides and said second converging sides of said one or more interior generally horizontal dividers, and wherein one or more of said brakes comprises a bore for receiving a fastener;
j) a lower plate adjoining said long side of said inferior generally horizontal divider, wherein said lower plate comprises one or more bores; and
k) an upper plate adjoining said long side of said superior generally horizontal divider, wherein said upper plate comprises one or more bores.

2. The implant of claim 1 further comprising a plurality of ties contacting said universal posts.

3. The implant of claim 2 wherein said first universal corner post is angled at about ninety degrees to simultaneously connect with said first converging sides and corresponding said inward short sides of said generally horizontal dividers, and wherein said second universal corner post is angled at about ninety degrees to simultaneously connect with said second converging sides and corresponding said inward short sides of said generally horizontal dividers.

4. The implant of claim 3, where said lower plate depends downward from said inferior generally horizontal divider and said upper plate extends upward from said superior generally horizontal divider.

5. An implant capable of fitting into a cavity surgically created between a superior vertebra and an inferior vertebra, said implant comprising:
a) a trapezoidal base comprising:
i) a short side;
ii) a long side;
iii) a first converging side creating a first corner with said short side and a third corner with said long side;
iv) a second converging side creating a second corner with said short side and a fourth corner with said long side; and
v) an aperture bounded by inner edges of said sides;
b) a first corner post extending vertically from said first corner;
c) a second corner post extending vertically from said second corner;
d) a third corner post extending vertically from said third corner;
e) a fourth corner post extending vertically from said fourth corner;
f) a top attached to said vertical posts further comprising an opening corresponding to said base's aperture;
g) one or more generally parallel dividers intermediate between said trapezoidal base and said top attached to said vertical posts; each generally parallel divider positioned between said base and said top, wherein said one or more generally parallel dividers, said base and said top form one or more receptacles capable of receiving osteogenic substances, and wherein, prior to addition of osteogenic substances into said one or more receptacles, arrangement of said one or more generally parallel dividers, said vertical posts, said base and said top includes openings allowing a surgeon to see through said implant;
h) one or more first side brakes, comprising a bore, attached to said third post and extending laterally beyond an outer edge of said first converging side of said implant;
i) one or more second side brakes, comprising a bore, attached to said fourth post and extending laterally beyond an outer edge of said second converging side of said implant; and
j) a first plate, comprising a bore, attached to an outward edge of said base or an outward edge of said top.

6. The implant of claim 5 further comprising a second plate, comprising a bore, attached to an outward edge of said base or an outward edge of said top not having said first plate attached thereto.

7. The implant of claim 6 further comprising:
a) one or more vertical posts extending between said base and said top; and
b) a plurality of ties contacting said corner posts and said one or more vertical posts.

8. The implant of claim 7 wherein said first corner post is angled at about ninety degrees to simultaneously connect with said first converging sides and said short sides of said one or more generally parallel dividers, and wherein said second corner post is angled at about ninety degrees to simultaneously connect with said second converging sides and short sides of said one or more generally parallel dividers.

9. The implant of claim 8, wherein said first plate and said second plate extend vertically outward from said implant.

10. A length of consecutively joined receptacles comprising peripheral openings a surgeon can see through prior to addition of osteogenic substances, wherein said length of consecutively joined receptacles comprises:
a) a series of trapezoidal dividers comprising first and second outward trapezoidal dividers and one or more inward trapezoidal dividers, wherein each said divider comprises:
i) an inward side;
ii) an outward side;
iii) a first side connected with said outward side and said inward side forming a first outward corner with said outward side and a first inward corner with said inward side;

iv) a second side connected with said outward side and said inward side forming a second outward corner with said outward side and a second inward corner with said inward side; and v) an aperture of similar area;

b) a first universal corner post contacting said first inward corners;

c) a second universal corner post contacting said second inward corners;

d) one or more universal posts contacting said first sides of said dividers; and e) one or more universal posts contacting said second sides of said dividers;

f) one or more first side brakes, comprising a bore, attached to said one or more first outward corners and extending laterally beyond said first sides; and g) one or more second side brakes, comprising a bore, attached to said one or more second outward corners and extending laterally beyond said second sides.

11. The length of consecutively joined receptacles of claim 10 further comprising:

a) a first plate, comprising a plurality of bores, attached to a superior trapezoidal divider of said generally vertical series of trapezoidal dividers; and b) a second plate, comprising a plurality of bores, attached to an inferior trapezoidal divider of said generally vertical series of trapezoidal dividers.

12. The length of consecutively joined receptacles of claim 11 further comprising a plurality of ties contacting said universal corner posts and said universal posts.

13. The length of consecutively joined receptacles of claim 12 wherein said first universal corner post is angled at about ninety degrees to simultaneously connect with said first sides and said short sides of said generally vertical series of trapezoidal dividers, and wherein said second universal corner post is angled at about ninety degrees to simultaneously connect with said second sides and short sides of said generally vertical series of trapezoidal dividers.

14. The length of consecutively joined receptacles of claim 13, wherein said first plate extends above said superior trapezoidal divider and said second plate depends below said inferior trapezoidal divider.

15. An implant capable of implantation into a surgically cavity created between a superior vertebra and an inferior vertebra, comprising peripheral openings a surgeon can see through prior to addition of osteogenic substances, wherein said implant comprises:

a) a series of trapezoidal dividers; said series comprising first and second outward trapezoidal dividers and one or more inward trapezoidal dividers, wherein each said trapezoidal divider comprises a perimeter of similar length;

b) a first universal corner post contacting first inward corners of said series;

c) a second universal corner post contacting second inward corners of said series;

d) one or more first universal posts contacting first sides of said series;

e) one or more second universal posts contacting second sides of said series;

f) one or more first side brakes attached to one or more outward edges of said series; said one or more first side brakes extending laterally beyond said first sides of said series, wherein at least one of said first side brakes comprises a bore for receiving a fastener; and g) one or more second side brakes attached to one or more outward edges of said series; said one or more second side brakes extending laterally beyond said second sides of said series, wherein at least one of said second side brakes comprises a bore for receiving a fastener.

16. The implant of claim 15 further comprising a plurality of ties contacting said universal corner posts and said universal posts.

17. The implant of claim 16 further comprising:

a) a first plate, comprising a bore, attached to an outward edge of a superior trapezoidal divider of said series; and b) a second plate, comprising a bore, attached to an outward edge of an inferior trapezoidal divider of said series.

18. The implant of claim 17, wherein said first plate extends above a superior trapezoidal divider of said series and said second plate depends below an inferior trapezoidal divider of said series.

19. The implant of claim 16, wherein said outward edge of said superior trapezoidal divider comprises a plurality of bores inset from a first side and a second side of said superior trapezoidal divider of said series, and wherein said outward edge of said inferior trapezoidal divider comprises a plurality of bores inset from a first side and a second side of said inferior trapezoidal divider of said series.

20. A generally vertical implant capable of implantation into a surgical cavity created between a superior vertebra and an inferior vertebra, comprising peripheral openings a surgeon can see through prior to addition of osteogenic substances, wherein said generally vertical implant comprises:

a) a series of trapezoidal dividers, wherein said series comprises first and second outward trapezoidal dividers and one or more inward trapezoidal dividers;

b) a first universal corner post contacting first inward corners of said series;

c) a second universal corner post contacting second inward corners of said series;

d) one or more first universal posts contacting first sides of said series;

e) one or more second universal posts contacting second sides of said series;

f) a first plate, comprising a bore, attached to an outward edge of trapezoidal divider of said series; and g) a second plate, comprising a bore, attached to an outward edge of an inferior trapezoidal divider of said series.

21. The implant of claim 20 further comprising:

a) one or more first side brakes attached to one or more outward edges of said series; said one or more first side brakes extending laterally beyond said first sides of said series, wherein at least one of said first side brakes comprises a bore for receiving a fastener; and b) one or more second side brakes attached to one or more outward edges of said series; said one or more second side brakes extending laterally beyond said second sides of said series, wherein at least one of said second side brakes comprises a bore for receiving a fastener.

22. The implant of claim 21 further comprising a plurality of ties contacting said universal corner posts and said universal posts.

23. The implant of claim 22, wherein said first plate extends above said superior trapezoidal divider of said series and said second plate depends below said inferior trapezoidal divider of said series.

* * * * *